(12) United States Patent
Miyazaki et al.

(10) Patent No.: US 7,939,540 B2
(45) Date of Patent: May 10, 2011

(54) 4-(3-BENZOYLAMINOPHENYL)-6,7-DIMETHOXY-2-METHYLAMINO-QUINAZOLINE DERIVATIVES

(75) Inventors: Kazuki Miyazaki, Tokyo (JP); Kazutomi Kusano, Tsukuba (JP); Yasutaka Takase, Tsukuba (JP); Osamu Asano, Tsukuba (JP); Manabu Shirato, Tsukuba (JP); Hisashi Wakita, Tsukuba (JP); Naoto Ishii, Tsukuba (JP); Takao Saeki, Tsukuba (JP); Tomoko Saeki, legal representative, Moriya (JP); Mai Saeki, legal representative, Moriya (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 1115 days.

(21) Appl. No.: 11/707,904

(22) Filed: Feb. 20, 2007

(65) Prior Publication Data

US 2007/0299094 A1  Dec. 27, 2007

Related U.S. Application Data

(60) Provisional application No. 60/774,620, filed on Feb. 21, 2006.

(51) Int. Cl.
*C07D 239/84* (2006.01)
*A61K 31/517* (2006.01)
*A61P 17/04* (2006.01)

(52) U.S. Cl. .................. 514/266.4; 544/292
(58) Field of Classification Search .............. 544/292; 514/266.4
See application file for complete search history.

(56) References Cited

U.S. PATENT DOCUMENTS

| | | | |
|---|---|---|---|
| 5,385,907 A | 1/1995 | Asakura et al. |
| 6,352,989 B1 | 3/2002 | Miyazaki et al. |
| 6,740,662 B1 | 5/2004 | Iwata et al. |
| 6,800,644 B2 | 10/2004 | Miyazaki et al. |
| 2006/0258703 A1 | 11/2006 | Shii et al. |
| 2009/0062539 A1 | 3/2009 | Yamamoto et al. |

FOREIGN PATENT DOCUMENTS

| | | |
|---|---|---|
| JP | 5-17481 A | 1/1993 |
| JP | 8-165251 A | 6/1996 |
| JP | 2001-192385 A | 7/2001 |
| JP | 2001-520196 A | 10/2001 |
| JP | 2005-29541 A | 2/2005 |
| JP | 2005-47909 A | 2/2005 |
| JP | 2005-529930 A | 10/2005 |
| JP | 2005-537262 A | 12/2005 |
| WO | WO 98/10767 A2 | 3/1998 |
| WO | WO-99/20280 A1 | 4/1999 |
| WO | WO-99/37622 A1 | 7/1999 |
| WO | WO 03/099278 A1 | 12/2003 |
| WO | WO 2004/006920 A1 | 1/2004 |
| WO | WO-2005/082865 A1 | 9/2005 |
| WO | WO 2006/093226 A1 | 9/2006 |
| WO | WO-2006/093226 A1 | 9/2006 |
| WO | WO 2007/097317 A1 | 8/2007 |
| WO | WO-2008/099887 A1 | 8/2008 |

OTHER PUBLICATIONS

Hanifin et al., Journal of Investigative Dermatology, vol. 107, No. 1, pp. 51-56, (1996).
Schmidt, MD et al., Journal of Allergy and Clinical Immunology, vol. 108, No. 4, pp. 530-536, (2001).
Yosipovitch et al., The Lancet, vol. 361, pp. 690-694, (2003).
Leung et al., The Lancet, vol. 361, pp. 151-160, (2003).
Klein, MD, et al., Archives Dermatology, vol. 135, pp. 1522-1525, (1999).
"The Fourth Series of Experimental Chemistry", vol. 1, Fundamental Procedure I, Edited by The Chemical Society of Japan, Maruzen Co., Ltd., p. 184-186, (1990).
English translations of the Notification of Transmittal of the International Preliminary Report on Patentability (Form PCT/IB/338), International Preliminary Report on Patentability (Form PCT/IB/373), Written Opinion of the International Searching Authority (Form PCT/ISA/237) issued Mar. 18, 2010 and International Search Report (Form PCT/ISA/210) issued Sep. 9, 2008 for International Application No. PCT/JP2008/064620.
Greene et al., "Protective Groups in Organic Synthesis," Third Edition, Protection for the Amino Group, 1999, pp. 518-525, pp. 551-555.
International Search Report mailed Sep. 9, 2008 in International Application No. PCT/JP2008/064621.
Extended European Search Report mailed Aug. 11, 2010 for Application No. 08827867.6.

(Continued)

*Primary Examiner* — Susanna Moore
(74) *Attorney, Agent, or Firm* — Birch, Stewart, Kolasch & Birch, LLP

(57) ABSTRACT

A compound represented by the following formula (I), salt thereof, or hydrate thereof, can effectively relieve itch caused by atopic disease or the like:

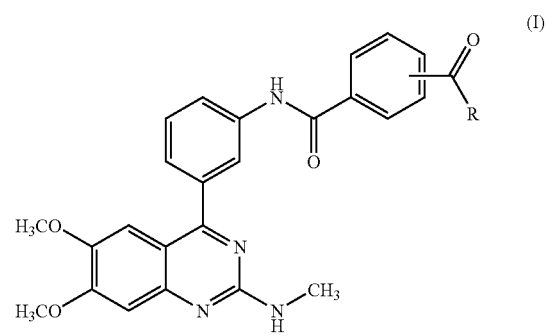

wherein R represents hydroxyl, $C_{1-6}$ alkoxy optionally substituted with $C_{1-6}$ alkoxy, or amino optionally substituted with $C_{1-6}$ alkyl.

17 Claims, 14 Drawing Sheets

OTHER PUBLICATIONS

International Preliminary Report on Patentability (Forms PCT/IB338 and PCT/IB/373) snd Written Opinion of the International Searching Authority (Form PCT/ISA/237), mailed Mar. 18, 2010, for International Application No. PCT/JP2008/064621.

Yakuji Nippo Limited, "Iyakuhin Tenkabutsu Jiten 2007" ("Pharmaceutical Excipients Dictionary 2007"), Edited by Japan Pharmaceutical Excipients Council, Jul. 25, 2007, pp. 279-280.

Yakuji Nippo Limited, "Iyakuhin Tenkabutsu Jiten 2007" ("Pharmaceutical Excipients Dictionary 2007"), Edited by Japan Pharmaceutical Excipients Council, Jul. 25, 2007, pp. 280-282 and 309.

English translations of the Notification of Transmittal of the International Preliminary Report on Patentability (Form PCT/IB/338), International Preliminary Report on Patentability (Form PCT/IB/373), and Written Opinion of the International Searching Authority(Form PCT/ISA/237) issued Aug. 27, 2009 for PCT/JP2008/052448.

4-(3-BENZOYLAMINOPHENYL)-6,7-DIMETHOXY-2-METHYLAMINO-QUINAZOLINE DERIVATIVES

RELATED APPLICATIONS

This application claims priority to U.S. Provisional Application No. 60/774,620 filed on Feb. 21, 2006, which is hereby incorporated by reference in its entirety.

BACKGROUND OF THE INVENTION

1. Field of the Invention

The present invention relates to novel compounds, 4-(3-benzoylaminophenyl)-6,7-dimethoxy-2-methylamino-quinazoline derivatives.

2. Related Background Art

In order to treat itch caused by atopic disease such as atopic dermatitis, an anti-inflammatory drug, such a steroid, an anti-histamine agent, or the like, is used as a therapeutic agent.

However, a steroid drug hardly has a direct anti-pruritic effect, and a reduction in itch by the above agent is only a secondary effect obtained as a result of inhibitory action on dermal inflammation. Accordingly, a certain period of time is required until such an anti-pruritic effect is obtained. In addition, the effectiveness of an anti-histamine agent is controvertible, and there are no reports clearly demonstrating its effectiveness on itch.

Itch is a typical symptom of atomic dermatitis. Persistent itch causes loss of concentration or insomnia, and thereby significantly impairs QOL. As described above, since a steroid drug requires a certain period of time for exhibiting its anti-pruritic effect and an anti-histamine agent is ineffective in many cases, itch is not still fully controlled by these drugs.

Moreover, an anti-pruritic agent effective not only for itch caused by atopic disease, but also for itch resistant to steroid drug and/or an anti-histamine agent, has not yet been discovered (refer to Non-Patent Documents 1 to 3).

By the way, the compound of the present invention that is represented by the formula (I) is within the scope of the compound of the invention disclosed in Patent Document 1.

However, the compound represented by the formula (I) is not specifically disclosed at all in the aforementioned Patent Document 1. The compound described in Patent Document 1, which has a structure similar to that of the compound represented by the formula (I), is the compound represented by the following structural formula:

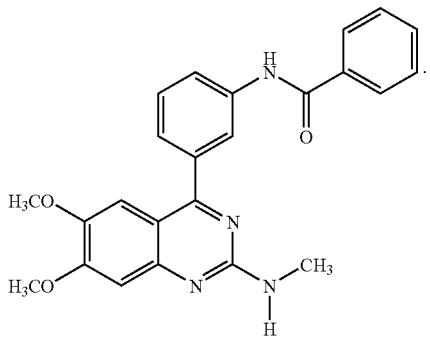

Furthermore, it is described that the compound of Patent Document 1 has PDE4 inhibitory action, and thus that the above compound has anti-inflammatory action based on PDE4 inhibitory action. Thus, Patent Document 1 describes that the above compound is effective for the treatment of psoriasis based on the anti-inflammatory action, but the above publication neither describes nor suggests application of the above compound to itch caused by atopic disease.

Still further, Patent Document 1 neither describes nor suggests that the compound described in the publication 1 is effective for itch on which a steroid drug or an anti-histamine agent is not effective.

[Non-Patent Document 1] Lancet 2003; 361: 690-694
[Non-Patent Document 2] Lancet 2003; 361: 151-160
[Non-Patent Document 3] Arch. Dermatol. 1999; 135: 1522-1525
[Patent Document 1] WO99/37622

SUMMARY OF THE INVENTION

It is an object of the present invention to provide a safe compound, which effectively acts on itch caused by atopic disease, or itch on which a steroid drug or the like is not effective, from the early stage.

As a result of intensive studies, the present inventors have found the present invention. That is to say, the present invention relates to:

(1) a compound represented by the formula (I), salt thereof, or hydrate thereof:

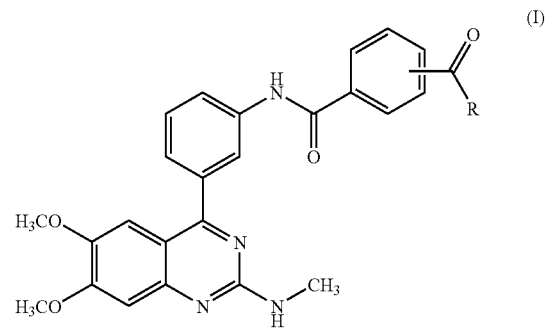

wherein R represents hydroxyl, $C_{1-6}$ alkoxy optionally substituted with $C_{1-6}$ alkoxy, or amino optionally substituted with $C_{1-6}$ alkyl;

(2) the compound, salt thereof, or hydrate thereof according to item (1) above, wherein R—C(=O)—, where R represents hydroxyl, $C_{1-6}$ alkoxy optionally substituted with $C_{1-6}$ alkoxy, or amino optionally substituted with $C_{1-6}$ alkyl, is bonded at the meta or para position;

(3) the compound, salt thereof, or hydrate thereof according to items (1) or (2) above, wherein R represents hydroxyl, $C_{1-3}$ alkoxy optionally substituted with $C_{1-3}$ alkoxy, or amino optionally substituted with $C_{1-3}$ alkyl;

(4) the compound, salt thereof, or hydrate thereof according to items (1) or (2) above, wherein R represents hydroxyl, methoxy, ethoxy, 1-propoxy, 2-propoxy, methoxyethoxy, amino, methylamino, dimethylamino, ethylamino, or diethylamino;

(5) methyl N-[3-(6,7-dimethoxy-2-methylaminoquinazolin-4-yl)phenyl]terephthalamic acid, salt thereof, or hydrate thereof;

ethyl N-[3-(6,7-dimethoxy-2-methylaminoquinazolin-4-yl)phenyl]terephthalamic acid, salt thereof, or hydrate thereof;

N-[3-(6,7-dimethoxy-2-methylaminoquinazolin-4-yl)phenyl]-N'-methylterephthalamide, salt thereof, or hydrate thereof;

isopropyl N-[3-(6,7-dimethoxy-2-methylaminoquinazolin-4-yl)phenyl]terephthalamic acid, salt thereof, or hydrate thereof;

isopropyl N-[3-(6,7-dimethoxy-2-methylaminoquinazolin-4-yl)phenyl]isophthalic acid, salt thereof, or hydrate thereof;

N-[3-(6,7-dimethoxy-2-methylaminoquinazolin-4-yl)phenyl]terephthalamic acid 2-methoxyethyl ester, salt thereof, or hydrate thereof; or N-[3-(6,7-dimethoxy-2-methylaminoquinazolin-4-yl)phenyl]isophthalamic acid 2-methoxyethyl ester, salt thereof, or hydrate thereof;

(6) methyl N-[3-(6,7-dimethoxy-2-methylaminoquinazolin-4-yl)phenyl]terephthalamic acid, salt thereof, or hydrate thereof;

(7) ethyl N-[3-(6,7-dimethoxy-2-methylaminoquinazolin-4-yl)phenyl]terephthalamic acid, salt thereof, or hydrate thereof;

(8) N-[3-(6,7-dimethoxy-2-methylaminoquinazolin-4-yl)phenyl]-N'-methylterephthalamide, salt thereof, or hydrate thereof;

(9) isopropyl N-[3-(6,7-dimethoxy-2-methylaminoquinazolin-4-yl)phenyl]terephthalamic acid, salt thereof, or hydrate thereof;

(10) isopropyl N-[3-(6,7-dimethoxy-2-methylaminoquinazolin-4-yl)phenyl]isophthalic acid, salt thereof, or hydrate thereof;

(11) N-[3-(6,7-dimethoxy-2-methylaminoquinazolin-4-yl)phenyl]terephthalamic acid 2-methoxyethyl ester, salt thereof, or hydrate thereof;

(12) N-[3-(6,7-dimethoxy-2-methylaminoquinazolin-4-yl)phenyl]isophthalamic acid 2-methoxyethyl ester, salt thereof, or hydrate thereof;

(13) a pharmaceutical composition comprising as an active ingredient, the compound, salt thereof, or hydrate thereof according to any one of items (1) to (12) above;

(14) an antipruritic agent for atopic disease, comprising as an active ingredient, the compound, salt thereof, or hydrate thereof according to any one of items (1) to (12) above;

(15) the antipruritic agent according to item (14) above, wherein the atopic disease is atopic dermatitis;

(16) an antipruritic agent for itch on which a steroid drug and/or an anti-histamine agent are not effective, comprising as an active ingredient, the compound, salt thereof, or hydrate thereof according to any one of items (1) to (12);

(17) the antipruritic agent according to any one of items (14) to (16) above, wherein the dosage form is an external preparation.

The present invention also relates to:

(P1) a compound represented by the formula (II), salt thereof, or hydrate thereof:

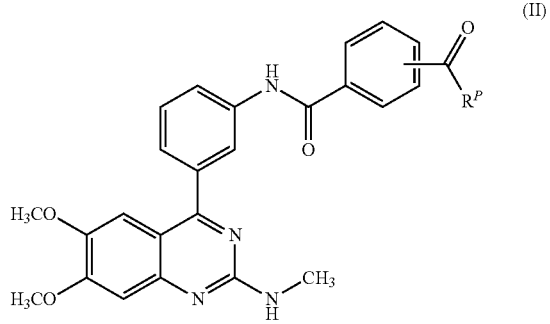

(II)

wherein $R^P$ represents hydroxyl, $C_{1-6}$ alkoxy, or amino optionally substituted with $C_{1-6}$ alkyl;

(P2) the compound, salt thereof, or hydrate thereof according to item (P1) above, wherein $R^P$—C(=O)—, where $R^P$ represents hydroxyl, $C_{1-6}$ alkoxy, or amino optionally substituted with $C_{1-6}$ alkyl, is bonded at the para position;

(P3) the compound, salt thereof, or hydrate thereof according to items (P1) or (P2) above, wherein $R^P$ represents hydroxyl, $C_{1-3}$ alkoxy or amino optionally substituted with $C_{1-3}$ alkyl;

(P4) the compound, salt thereof, or hydrate thereof according to items (P1) or (P2) above, wherein $R^P$ represents hydroxyl, methoxy, ethoxy, amino, methylamino, dimethylamino, ethylamino, or diethylamino;

(P5) methyl N-[3-(6,7-dimethoxy-2-methylaminoquinazolin-4-yl)phenyl]terephthalamic acid, salt thereof, or hydrate thereof;

ethyl N-[3-(6,7-dimethoxy-2-methylaminoquinazolin-4-yl)phenyl]terephthalamic acid, salt thereof, or hydrate thereof; or N-[3-(6,7-dimethoxy-2-methylaminoquinazolin-4-yl)phenyl]-N'-methylterephthalamide, salt thereof, or hydrate thereof;

(P6) a pharmaceutical composition comprising as an active ingredient, the compound, salt thereof, or hydrate thereof according to any one of items (P1) to (P5) above;

(P7) an antipruritic agent for atopic disease, comprising as an active ingredient, the compound, salt thereof, or hydrate thereof according to any one of items (P1) to (P5) above;

(P8) the antipruritic agent according to item (P7) above, wherein the atopic disease is atopic dermatitis;

(P9) an antipruritic agent for itch on which a steroid drug and/or an anti-histamine agent are not effective, comprising as an active ingredient, the compound, salt thereof, or hydrate thereof according to any one of items (P1) to (P5);

(P10) the antipruritic agent according to any one of items (P7) to (P9) above, wherein the dosage form is an external preparation.

From the results of the tests as described below, it was found that the compound of the present invention has an excellent antipruritic effect and also has an excellent effect in terms of metabolism. Accordingly, the compound of the present invention is useful as an antipruritic agent for itch caused by atopic disease, inter alia atopic dermatitis, or itch on which a steroid drug and/or an anti-histamine agent are not effective.

DESCRIPTION OF THE PREFERRED EMBODIMENTS

Figure 1:
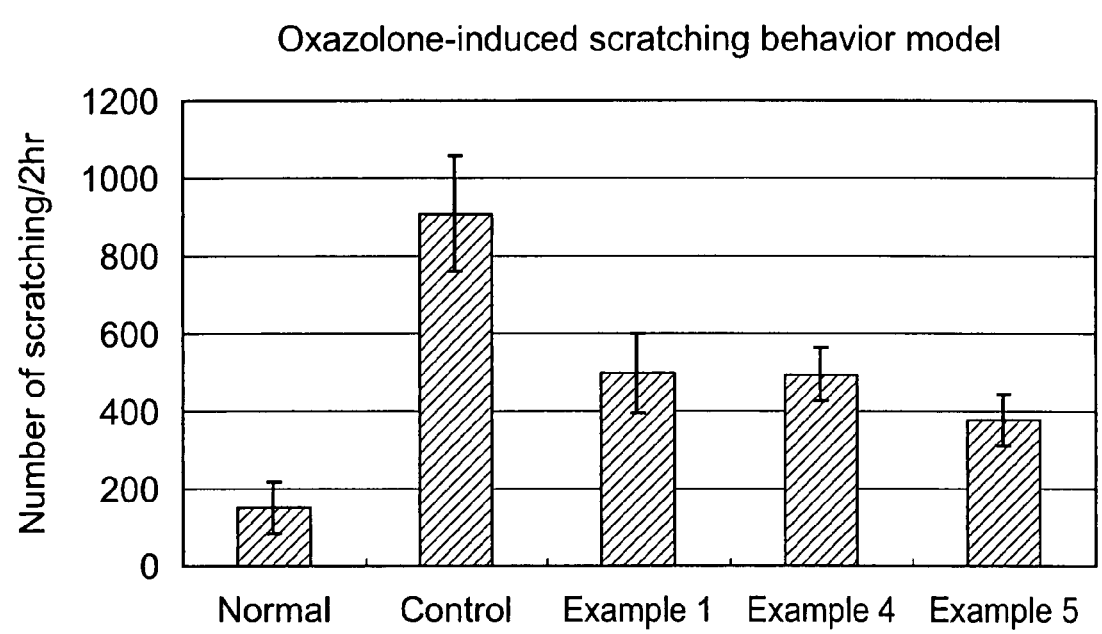
FIG. 1 shows the numbers of scratching behaviors of oxazolone-induced mice (Examples 1, 4 and 5).

The present invention will be described in detail below.

In the present specification, the structural formula of a compound may indicate a certain type of isomer, as a matter of convenience. The present invention includes all isomers generated because of the structure of a compound, such as a geometric isomer, an optical isomer, a stereoisomer, or a tautomer, and an isomeric mixture. Thus, the compound of the present invention is not limited to the descriptions of a formula provided as a matter of convenience, but it may be either one of such isomers or a mixture thereof. Accordingly, an optically active form and a racemic form may exist in the compound of the present invention. In the present invention, such an optically active form and a racemic form are not limited, and any of them are included. In addition, a crystal polymorphism may also exist in the compound of the present invention. Such a crystal polymorphism is not limited either, and the present invention may be either a single crystal form or a mixture thereof. Moreover, the present invention also includes an amorphous form, and the compound of the present invention includes an anhydrate and a hydrate. Furthermore, the present invention also includes so-called a metabolite, which is generated as a result of in vivo metabolism (oxidation, reduction, hydrolysis, conjugation, etc.) of the compound (I) of the present invention. Still further, a compound (so-called a prodrug), which generates the compound (I) of the present invention as a result of in vivo metabolism (oxidation, reduction, hydrolysis, conjugation, etc.), is also included in the present invention.

The definitions of terms, symbols, and others used in the present specification will be explained below, and the present invention will be described in detail below.

The term "$C_{1-6}$ alkyl" is used in the present specification to mean a linear or branched-chain alkyl group containing 1 to 6 carbon atoms. Specific examples of $C_{1-6}$ alkyl may include methyl, ethyl, 1-propyl (n-propyl), 2-propyl (i-propyl), 2-methyl-1-propyl (i-butyl), 2-methyl-2-propyl (t-butyl), 1-butyl (n-butyl), 2-butyl (s-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1-butyl, 2,2-dimethyl-1-butyl, 2-ethyl-1-butyl, 3,3-dimethyl-2-butyl, and 2,3-dimethyl-2-butyl.

Preferred examples may include $C_{1-3}$ alkyl such as methyl, ethyl, 1-propyl (n-propyl), 2-propyl (i-propyl), 2-methyl-1-propyl (i-butyl), 2-methyl-2-propyl (t-butyl), 1-butyl (n-butyl), or 2-butyl (s-butyl). More preferred examples may include methyl and ethyl.

The term "$C_{1-6}$ alkoxy" is used in the present specification to mean an oxy group to which the above defined "$C_{1-6}$ alkyl" binds. Specific examples of $C_{1-6}$ alkoxy may include methoxy, ethoxy, 1-propoxy, 2-propoxy, 2-methyl-1-propoxy, 2-methyl-2-propoxy, 1-butoxy, 2-butoxy, 1-pentoxy, 2-pentyloxy, 3-pentyloxy, 2-methyl-1-butoxy, 3-methyl-1-butoxy, 2-methyl-2-butoxy, 3-methyl-2-butoxy, 2,2-dimethyl-1-propoxy, 1-hexyloxy, 2-hexyloxy, 3-hexyloxy, 2-methyl-1-pentoxy, 3-methyl-1-pentyloxy, 4-methyl-1-pentoxy, 2-methyl-2-pentoxy, 3-methyl-2-pentoxy, 4-methyl-2-pentoxy, 2-methyl-3-pentyloxy, 3-methyl-3-pentyloxy, 2,3-dimethyl-1-butoxy, 3,3-dimethyl-1-butoxy, 2,2-dimethyl-1-butoxy, 2-ethyl-1-butoxy, 3,3-dimethyl-2-butoxy, and 2,3-dimethyl-2-butoxy.

Preferred examples may include $C_{1-3}$ alkoxy such as methoxy, ethoxy, 1-propoxy, and 2-propoxy. A more preferred example is methoxy.

In addition, examples of "$C_{1-6}$ alkoxy optionally substituted with $C_{1-6}$ alkoxy" or "$C_{1-3}$ alkoxy optionally substituted with $C_{1-3}$ alkoxy" in the definitions of R may include methoxymethoxy, ethoxymethoxy, methoxyethoxy, and ethoxyethoxy.

Examples of "amino optionally substituted with $C_{1-6}$ alkyl" in the present specification may include amino, mono-$C_{1-6}$ alkylamino that is substituted with the aforementioned $C_{1-6}$ alkyl (for example, methylamino, ethylamino, t-butylamino, etc.), and di-$C_{1-6}$ alkylamino (for example, dimethylamino, diethylamino, methylethylamino, etc.).

Preferred examples may include amino, mono-$C_{1-3}$ alkylamino, and di-$C_{1-3}$ alkylamino. More preferred examples may include amino and monomethylamino.

The type of a "salt" used in the present specification is not particularly limited, as long as it forms a salt together with the compound of the present invention and it is pharmacologically acceptable. Examples of such a salt may include an inorganic acid salt, an organic acid salt, an inorganic basic salt, an organic basic salt, and an acidic or basic amino acid salt.

Preferred examples of an inorganic acid salt may include hydrochloride, hydrobromide, sulfate, nitrate, and phosphate. Preferred examples of an organic acid salt may include acetate, succinate, fumarate, maleate, tartrate, citrate, lactate, stearate, benzoate, methanesulfonate, ethanesulfonate, p-toluenesulfonate, and benzenesulfonate.

Preferred examples of an inorganic basic salt may include: alkaline metal salts such as a sodium salt or a potassium salt; alkaline-earth metal salts such as a calcium salt or a magnesium salt; aluminum salts; and ammonium salts. Preferred examples of an organic basic salt may include a diethylamine salt, a diethanolamine salt, a meglumine salt, and an N,N'-dibenzylethylenediamine salt.

Preferred examples of an acidic amino acid salt may include aspartate and glutamate. Preferred examples of a basic amino acid salt may include an arginine salt, a lysine salt, and an ornithine salt.

In the present specification, R—C(=O) in the formula (I) (wherein R represents hydroxyl, $C_{1-6}$ alkoxy optionally substituted with $C_{1-6}$ alkoxy or amino optionally substituted with $C_{1-6}$ alkyl) may be bonded at any substitution positions, namely, the ortho, meta, or para position on a benzene ring to which it binds. It is preferably bonded at the meta or para position. That is to say, a compound represented by the following formula (I') or (I'') is preferable:

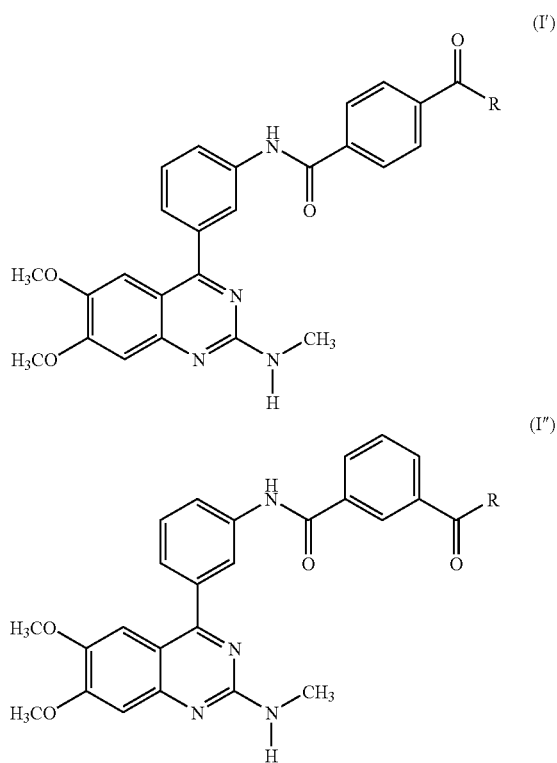

[wherein R has the same definitions as those described above]. More preferred examples of such a compound may include:

methyl N-[3-(6,7-dimethoxy-2-methylaminoquinazolin-4-yl)phenyl]terephthalamic acid, salt thereof, or hydrate thereof;

ethyl N-[3-(6,7-dimethoxy-2-methylaminoquinazolin-4-yl)phenyl]terephthalamic acid, salt thereof, or hydrate thereof; and N-[3-(6,7-dimethoxy-2-methylaminoquinazolin-4-yl)phenyl]-N'-methylterephthalamide, salt thereof, or hydrate thereof.

The term "atopic disease" is used in the present specification to mean atopic dermatitis, urticaria, bronchial asthma, allergic rhinitis, allergic conjunctivitis, etc.

When a compound of this invention is to be used as a medicament, it is normally compounded with suitable pharmaceutical ingredients to prepare pharmaceutical products for use. Notwithstanding, the use of a drug substance form of the compound of the invention as a medicament should not be negated.

The pharmaceutical ingredients may include excipients, binders, lubricants, disintegrating agents, coloring agents, taste correctives, emulsifiers, surfactants, dissolving aids, suspending agents, isotonizing agents, buffering agents, preservatives, antioxidants, stabilizers, absorption enhancers, and the like, all of which are generally used in medicaments. If desired, these agents may be combined for use.

The excipients may include, for example, lactose, white soft sugar, glucose, corn starch, mannitol, sorbitol, starch, alpha starch, dextrin, crystalline cellulose, light silicic anhydride, aluminum silicate, calcium silicate, magnesium aluminometasilicate, calcium hydrogenphosphate, and the like.

The binders may include, for example, polyvinyl alcohol, methylcellulose, ethylcellulose, gum Arabic, tragacanth, gelatin, shellac, hydroxypropylmethylcellulose, hydroxypropylcellulose, carboxymethylcellulose sodium, polyvinylpyrrolidone, macrogol, and the like.

The lubricants may include, for example, magnesium stearate, calcium stearate, sodium stearyl fumarate, talc, polyethylene glycol, colloidal silica, and the like.

The disintegrating agents may include, for example, crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch, carboxymethyl starch sodium, and the like.

The coloring agents may include iron sesquioxide, yellow iron sesquioxide, carmine, caramel, beta-carotene, titanium oxide, talc, riboflavin sodium phosphate, yellow aluminum lake, and the like, which have been approved as additives for medicaments.

The taste correctives agents may include cocoa powder, menthol, aromatic powder, mentha oil, borneol, powdered cinnamon bark, and the like The emulsifiers or the surfactants may include stearyl triethanolamine, sodium lauryl sulfate, lauryl aminopropionic acid, lecithin, glycerin monostearate, sucrose fatty acid ester, glycerin fatty acid ester, and the like.

The dissolving aids may include polyethylene glycol, propylene glycol, benzyl benzoate, ethanol, cholesterol, triethanolamine, sodium carbonate, sodium citrate, Polysorbate 80, nicotinamide, and the like.

The suspending agents may include, in addition to the surfactants, hydrophilic polymers such as polyvinyl alcohol, polyvinylpyrrolidone, methylcellulose, hydroxymethylcellulose, hydroxyethylcellulose, and hydroxypropylcellulose.

The isotonizing agents may include glucose, sodium chloride, mannitol, sorbitol and the like.

The buffering agents may include the buffers of phosphate, acetate, carbonate, citrate and the like.

The preservatives may include methylparaben, propylparaben, chlorobutanol, benzyl alcohol, phenethyl alcohol, dehydroacetic acid, sorbic acid and the like.

The antioxidants may include sulfite, ascorbic acid, alpha-tocopherol and the like.

The stabilizers may include those generally used in medicaments.

The absorption enhancers may include those generally used in medicaments.

The pharmaceutical products described above may include: oral agents such as tablets, powders, granules, capsules, syrups, troches, and inhalations; external preparations such as suppositories, ointments, ophthalmic ointments, tapes, ophthalmic solutions, nasal drops, ear drops, poultices, and lotions; and injections. A preferred formulation is an external preparation, which directly acts on affected area.

The oral agents may appropriately be combined with the auxiliaries described above to form preparations. In addition, the surfaces of the agents may be coated if necessary.

The external preparations may appropriately be combined with the auxiliaries, in particular, excipients, binders, taste correctives, emulsifiers, surfactants, dissolving aids, suspending agents, isotonizing agents, preservatives, antioxidants, stabilizers, or absorption enhancers to form the preparations.

The injections may appropriately be combined with the auxiliaries, in particular, emulsifiers, surfactants, dissolving aids, suspending agents, isotonizing agents, preservatives, antioxidants, stabilizers, or absorption enhancers to form the preparations.

The dosage of the pharmaceutical of the present invention is different depending on the degree of symptoms, age, sex, body weight, dosage form, the type of salts, difference in sensitivity to the agent, the specific type of disease, or the like. In general, in the case of oral administration, the dosage of the pharmaceutical of the present invention is between approximately 30 µg and 10 g (preferably between 0.1 mg and 100 mg) per adult per day. In the case of an external preparation, it is between 30 µg and 20 g (preferably between 100 µg and 10 g) per adult per day. In the case of an injection, it is between 30 µg and 1 g (preferably between 100 µg and 500 mg) per adult per day. The aforementioned dosage is used per day as a single administration, or divided over 2 to 6 administrations.

Raw material compounds and various types of reagents used in production of the compound of the present invention may form a salt, a hydrate, or a solvate. Such raw material compounds and reagents are different depending on a starting material, a solvent used, or the like. The types of such raw material compounds and reagents are not particularly limited, as long as they do not inhibit the reaction. A solvent used is also different depending on starting raw materials, reagents, or the like. Needless to say, the type of such a solvent is not particularly limited, as long as it does not inhibit the reaction and it dissolves starting materials to a certain extent. When the compound (I) of the present invention is obtained in a free form, such a free form can be converted to a salt that may be formed by the above compound (I), or a hydrate thereof, according to common methods.

The compound (I) of the present invention is obtained in a form of a salt or hydrate of the compound (I), these components can be converted to a free form of the above compound (I) according to common methods.

In addition, various isomers (for example, a geometric isomer, an optical isomer, a rotational isomer, a stereoisomer, a tautomer, etc.) obtained relative to the compound (I) of the present invention can be purified and isolated by ordinary separation means such as recrystallization, diastereomer salt method, enzyme division method, various types of chromatography (for example, thin-layer chromatography, column chromatography, gas chromatography, etc.).

Next, a method for producing the compound of the present invention that is represented by the formula (I) will be described.

The compound represented by the formula (I) can be produced by method A, method B, or method C as described below. Further, the compound can also be produced by method D, which is described in WO99/37622.

Method A, method B, and method C will be described in detail below. However, the production method of the compound of the present invention is not limited thereto.

(Method A)

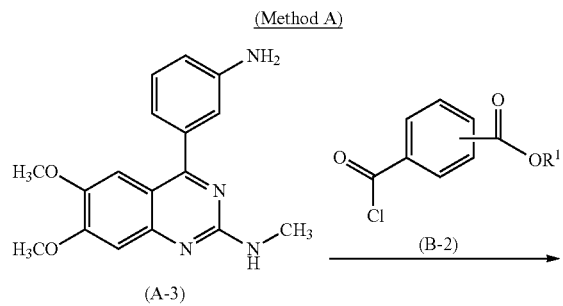

(A-3)  (B-2)

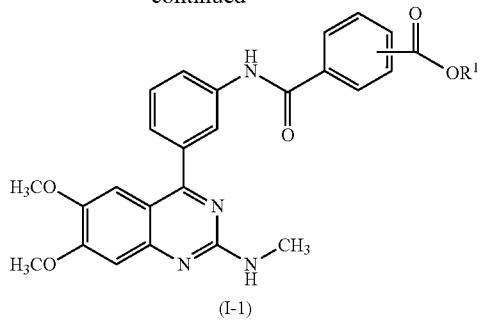

(I-1)

[wherein $R^1$ represents $C_{1-6}$ alkyl.]

Method A is a method of allowing a compound (A-3) to react with a compound (B-2) that is acid chloride in an inert solvent in the presence or absence of a base, so as to produce the compound (I-1) of the present invention.

As such a compound (B-2), a known compound, a commercially available compound, or a compound that can easily be produced from a commercially available compound by a method that is generally carried out by those skilled in the art, can be used. Examples of such a compound (B-2) may include 4-chlorocarbonyl benzoic acid methyl ester and the like.

The compound (B-2) can be used in an amount of 1 to 10 times, and preferably 1 to 2 times the molar equivalent of the compound (A-3).

The type of a solvent used is not particularly limited, as long as it dissolves starting substances to a certain extent and it does not inhibit the reaction in the present step. Examples of a solvent may include: aromatic hydrocarbons such as toluene, benzene, or xylene; ethers such as diethyl ether, tetrahydrofuran, dimethoxyethane, or dioxane; halogenated hydrocarbons such as dichloromethane, chloroform, 1,2-dichloroethane, or carbon tetrachloride; organic bases such as pyridine, or 2-, 3- or 4-picoline; water; and a mixture of these solvents. Preferred examples are tetrahydrofuran or pyridine.

The type of a base used herein is not particularly limited, as long as a compound of interest can be obtained and non-separable by-products are not generated. Examples of a base may include: inorganic bases such as sodium carbonate, potassium carbonate, sodium hydrogencarbonate, potassium hydrogencarbonate, or cesium carbonate; and organic bases such as pyridine or triethylamine. A preferred example is pyridine.

The aforementioned base can be used in an amount of 1 to 10 times, and preferably 1 to 4 times the molar equivalent of the compound (A-3).

The reaction temperature depends on a solvent and a reagent used. It is generally between −30° C. and 180° C., and preferably between 0° C. and 100° C.

The reaction time depends on a solvent used and the reaction temperature. It is generally between 0.5 and 200 hours, and preferably between 1 and 100 hours.

(Method B)

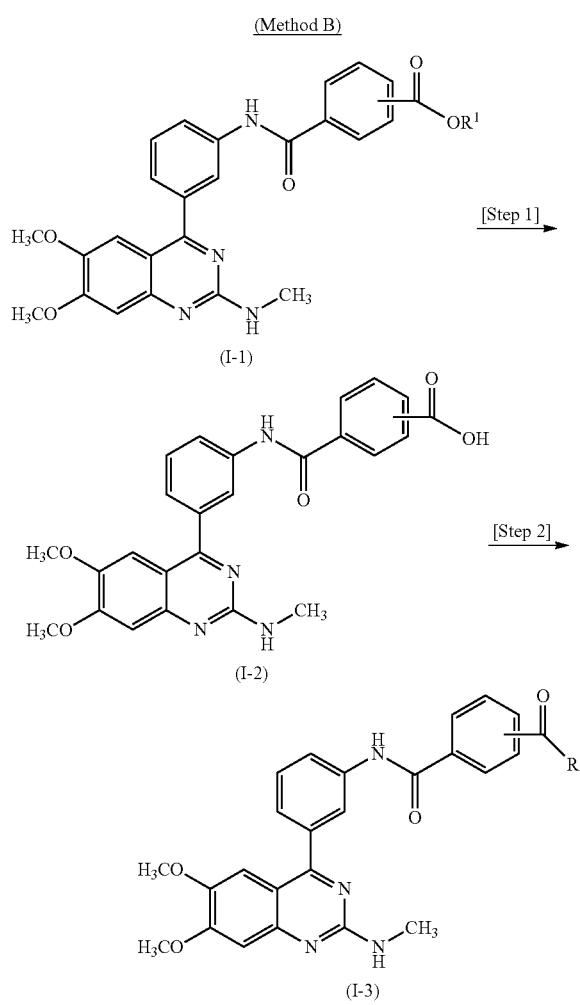

[wherein R[1] has the same definitions as those described above, and R' represents $C_{1-6}$ alkoxy optionally substituted with $C_{1-6}$ alkoxy, or amino optionally substituted with $C_{1-6}$ alkyl.]

Method B is a method, which comprises: step 1 of obtaining a carboxylic acid compound (I-2) as a result of the hydrolysis reaction of an ester compound (I-1); and step 2 of esterifying or amidating the above carboxylic acid compound (I-2), so as to obtain the compound (I-3) of the present invention.

<Step 1: Hydrolysis Reaction>

The compound (I-2) is obtained as a result of the basic hydrolysis reaction of the compound (I-1) in an inert solvent.

The type of a solvent used is not particularly limited, as long as it dissolves starting substances to a certain extent and it does not inhibit the reaction in the present step. Examples of a solvent may include: aromatic hydrocarbons such as toluene, benzene, or xylene; ethers such as diethyl ether, tetrahydrofuran, dimethoxyethane, or dioxane; alcohols such as methanol, ethanol, n-propanol, isopropanol, n-butanol, t-butanol, or ethylene glycol; water; and a mixture of these solvents. Preferred examples are methanol or tetrahydrofuran.

The type of a base used herein is not particularly limited, as long as a compound of interest can be obtained and non-separable by-products are not generated. Examples of a base may include: inorganic bases such as sodium hydroxide, potassium hydroxide, lithium hydroxide, sodium carbonate, potassium carbonate, sodium hydrogencarbonate, potassium hydrogencarbonate, cesium carbonate, or an aqueous solution thereof; and organic bases such as pyridine or triethylamine. A preferred example is a sodium hydroxide aqueous solution.

The aforementioned base can be used in an amount of 1 to 100 times, and preferably 1 to 20 times the molar equivalent of the compound (I-1).

The reaction temperature depends on a solvent and a reagent used. It is generally between −30° C. and 180° C., and preferably between 0° C. and 100° C.

The reaction time depends on a solvent used and the reaction temperature. It is generally between 0.5 and 200 hours, and preferably between 1 and 100 hours.

<Step 2: Esterification or Amidation of Compound (I-2)>

The compound (I-3) is obtained as a result of the condensation reaction of the compound (I-2) with corresponding alcohol or amine, using a condensing agent, in an inert solvent in the presence or absence of a base.

As such corresponding alcohol or amine, a known compound, a commercially available compound, or a compound that can easily be produced from a commercially available compound by a method that is generally carried out by those skilled in the art, can be used. Examples of such a compound may include methanol, ethanol, and methylamine.

The above alcohol or amine can be used in an amount of 1 to 10 times, and preferably 1 to 3 times the molar equivalent of the compound (I-2).

The type of a solvent used is not particularly limited, as long as it dissolves starting substances to a certain extent and it does not inhibit the reaction in the present step. Examples of a solvent may include: aromatic hydrocarbons such as toluene, benzene, or xylene; ethers such as diethyl ether, tetrahydrofuran, dimethoxyethane, or dioxane; esters such as methyl acetate, ethyl acetate, propyl acetate, or diethyl carbonate; amides such as formamide, dimethylformamide, dimethylacetamide, hexamethylphosphoramide, or N-methylpyrrolidone; and a mixture of these solvents. A preferred example is dimethylformamide.

The type of a condensing agent used herein is not particularly limited, as long as a compound of interest can be obtained and non-separable by-products are not generated. Examples of a condensing agent may include: carbodiimides such as dicyclohexylcarbodiimide (DCC) or N-(3-dimethylaminopropyl)-N'-ethylcarbodiimide (EDC: WSC); and phosphine condensing agents such as benzotriazol-1-yloxytris(dimethylamino)phosphonium hexafluorophosphate (BOP) or diethyl cyanophosphonate (DEPC). A preferred example of a condensing agent used herein is WSC.

The aforementioned condensing agent can be used in an amount of 1 to 10 times, and preferably 1 to 3 times the molar equivalent of the compound (I-2).

The type of a base used herein is not particularly limited, as long as a compound of interest can be obtained and non-separable by-products are not generated. Examples of a base may include: aqueous solutions of inorganic bases such as sodium hydroxide, potassium hydroxide, lithium hydroxide, sodium carbonate, potassium carbonate, sodium hydrogencarbonate, potassium hydrogencarbonate, or cesium carbonate; and organic bases such as pyridine or triethylamine. A preferred example is triethylamine.

The aforementioned base can be used in an amount of 1 to 10 times, and preferably 1 to 3 times the molar equivalent of the compound (I-2).

If desired, 4-dimethylaminopyridine or 1-hydroxybenzotriazole may be used as an additive for accelerating the reaction.

The aforementioned additive can be used in an amount of 0.1 to 10 times, and preferably 0.1 to 3 times the molar equivalent of the compound (I-2)

The reaction temperature is not particularly limited. It is generally between −30° C. and 180° C., and preferably between 0° C. and 80° C.

The reaction time is not particularly limited. It is generally between 0.5 and 200 hours, and preferably between 1 and 100 hours.

It is to be noted that the present step can also be carried out by the mixed anhydride method using ethyl chloroformate, ethyl acetate, or the like.

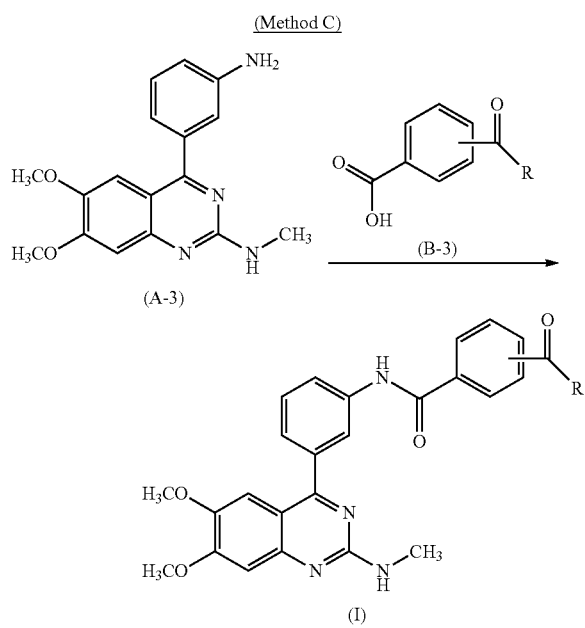

[wherein R has the same definitions as those described above.]

This method is a method of subjecting the compound (A-3) to a condensation reaction with corresponding carboxylic acid (B-3), using a condensing agent, in an inert solvent in the presence or absence of a base, so as to produce the compound (I).

As such a compound (B-3), a known compound, a commercially available compound, or a compound that can easily be produced from a commercially available compound by a method that is generally carried out by those skilled in the art, can be used. An example of such a compound (B-3) is terephthalic acid monomethyl ester, which can be easily produced from terephthalic acid.

The compound (B-3) can be used in an amount of 1 to 10 times, and preferably 1 to 3 times the molar equivalent of the compound (A-3).

The type of a solvent used is not particularly limited, as long as it dissolves starting substances to a certain extent and it does not inhibit the reaction in the present step. Examples of a solvent may include: aromatic hydrocarbons such as toluene, benzene, or xylene; ethers such as diethyl ether, tetrahydrofuran, dimethoxyethane, or dioxane; esters such as methyl acetate, ethyl acetate, propyl acetate, or diethyl carbonate; amides such as formamide, dimethylformamide, dimethylacetamide, hexamethylphosphoramide, or N-methylpyrrolidone; and a mixture of these solvents. A preferred example is dimethylformamide.

The type of a condensing agent used herein is not particularly limited, as long as a compound of interest can be obtained and non-separable by-products are not generated. Examples of a condensing agent may include: carbodiimides such as dicyclohexylcarbodiimide (DCC) or N-(3-dimethylaminopropyl)-N'-ethylcarbodiimide (EDC: WSC); and phosphine condensing agents such as benzotriazol-1-yloxy-tris(dimethylamino)phosphonium hexafluorophosphate (BOP) or diethyl cyanophosphonate (DEPC). A preferred example of a condensing agent used herein is WSC.

The aforementioned additive can be used in an amount of 1 to 10 times, and preferably 1 to 3 times the molar equivalent of the compound (A-3).

The type of a base used herein is not particularly limited, as long as a compound of interest can be obtained and non-separable by-products are not generated. Examples of a base may include: aqueous solutions of inorganic bases such as sodium hydroxide, potassium hydroxide, lithium hydroxide, sodium carbonate, potassium carbonate, sodium hydrogencarbonate, potassium hydrogencarbonate, or cesium carbonate; and organic bases such as pyridine or triethylamine. A preferred example is triethylamine.

The aforementioned base can be used in an amount of 1 to 10 times, and preferably 1 to 3 times the molar equivalent of the compound (A-3).

If desired, 4-dimethylaminopyridine or 1-hydroxybenzotriazole may be used as an additive for accelerating the reaction.

The aforementioned additive can be used in an amount of 0.1 to 10 times, and preferably 0.1 to 3 times the molar equivalent of the compound (A-3)

The reaction temperature depends on a solvent and a reagent used. It is generally between −30° C. and 180° C., and preferably between 0° C. and 80° C.

The reaction time depends on a solvent used and the reaction temperature. It is generally between 0.5 and 200 hours, and preferably between 1 and 100 hours.

It is to be noted that the present step can also be carried out by the mixed anhydride method using ethyl chloroformate, ethyl acetate, or the like.

(Production Method of Intermediate)

The compound (A-3) that is an intermediate commonly used in methods A, B, and C, can be produced by the method disclosed in production example 7 of WO99/37622. Other than the above method, the compound (A-3) is synthesized by the following intermediate production method, for example:

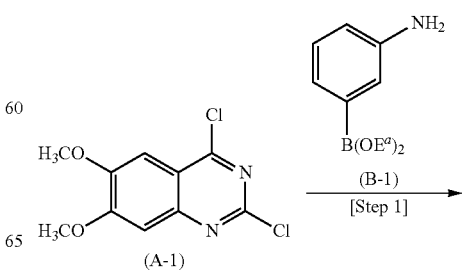

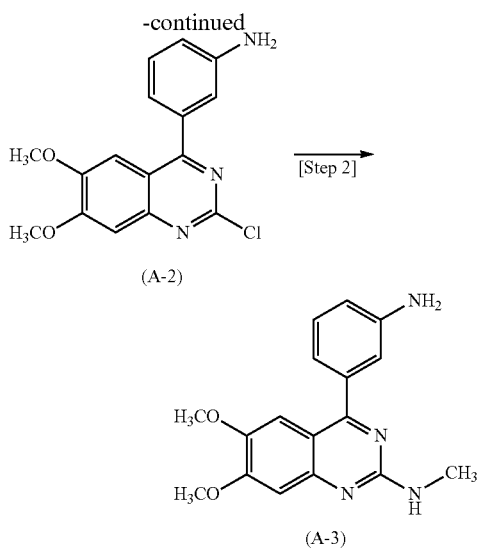

[wherein $E^\alpha$ independently represents hydrogen or $C_{1-6}$ alkyl, or two $E^\alpha$ form together $C_{2-3}$ alkylene optionally substituted with methyl.]

The present production method comprises: step 1 of subjecting a compound (A-1) and a compound (B-1) acting as a boron metal reagent to a coupling reaction like Suzuki reaction, in an inert solvent, in the presence of a palladium(0) catalyst, under the atmosphere of inert gas or without such atmosphere, in the presence or absence of a base, and in the presence or absence of additives, so as to obtain a compound (A-2); and step 2 of converting the chloro group of the compound (A-2) to a methylamino group, so as to produce a compound (A-3) that is the intermediate of the compound of the present invention.

<Step 1: Coupling Reaction>

The present step is a step of allowing the compound (A-1) to react with the compound (B-1) in an inert solvent, in the presence of a palladium(0) catalyst, in the presence of a base, in the presence or absence of additives, and under the atmosphere of inert gas or without such atmosphere, so as to produce the intermediate compound (A-2).

The present step can be carried out in accordance with publications described in S. P. Stanforth, Tetrahedron (1998), 54, 263, N. Miyaura, A. Suzuki, Chem. Rev. (1995), 95, 2457, etc. More specifically, the present step can be carried out, referring to the reaction conditions, operations conducted after the reaction, a purification method, etc., which are described in production example 1 below.

The compound (A-1) is a known compound. A commercially available product can be purchased and used as the compound (A-1).

The type of the compound (B-1) used for coupling is not particularly limited, as long as a compound of interest can be obtained and non-separable by-products are not generated. Examples of the compound (B-1) may include 3-aminophenyl boronic acid, a ½ sulfate thereof, and a hydrate thereof. Preferably, 3-aminophenyl boronic acid ½ sulfate is used.

The compound (B-1) can be used in an amount of 0.5 to 10 times, and preferably 0.5 to 1.5 times the molar equivalent of the compound (A-1).

The type of a solvent used is not particularly limited, as long as it dissolves starting substances to a certain extent and it does not inhibit the reaction in the present step. Specific examples of a solvent may include: amides such as formamide, dimethylformamide, dimethylacetamide, hexamethylphosphoric triamide, or N-methylpyrrolidone; aromatic hydrocarbons such as toluene, benzene, xylene, or mesitylene; ethers such as diethyl ether, diisopropyl ether, tetrahydrofuran, dioxane, dimethoxyethane, or diethylene glycol dimethyl ether; alcohols such as methanol, ethanol, n-propanol, isopropanol, n-butanol, isobutanol, t-butanol, isoamyl alcohol, diethylene glycol, glycerin, octanol, cyclohexanol, or methyl cellosolve; nitriles such as acetonitrile or isobutyronitrile; sulfoxides such as dimethyl sulfoxide or sulfolane; esters such as methyl acetate, ethyl acetate, propyl acetate, or diethyl carbonate; water; and a mixed solvent of these solvents. Preferred examples may include toluene, tetrahydrofuran, ethyl acetate, water, and a mixed solvent of these solvents.

The type of a palladium(0) catalyst used is not particularly limited, as long as a compound of interest can be obtained and non-separable by-products are not generated. Examples of a palladium(0) catalyst may include tetrakis(triphenylphosphine)palladium, tris(dibenzylideneacetone)dipalladium, bis(dibenzylideneacetone)palladium, bis(tri-t-butylphosphine)palladium, palladium black, various types of palladium complexes that become palladium(0) precursors as described below, and a palladium(0) catalyst generated in a reaction system as a result of combination with various types of ligands as described below.

That is to say, the types of various types of palladium complexes that become palladium(0) precursors are not particularly limited, as long as a compound of interest can be obtained and non-separable by-products are not generated. Specific examples of such palladium complexes may include palladium acetate, [1,1'-bis(diphenylphosphino)ferrocene]dichloropalladium, dichlorobis(tri-o-tolylphosphine)palladium, and dichlorobis(tricyclohexylphosphine)palladium. The type of a ligand is not particularly limited, as long as a compound of interest can be obtained and non-separable by-products are not generated. Specific examples of such a ligand may include 2,2'-bis(diphenylphosphino)-1,1'-binaphthyl (BINAP), 9,9-dimethyl-4,5-bis(diphenylphosphino)xanthene (Xantphos), tri-t-butylphosphine, tri(4-methylphenyl)phosphine, tri-2-furylphosphine, 2-(di-t-butylphosphino)biphenyl, 2-(dicyclohexylphosphino)biphenyl, tricyclohexylphosphine, 2-dicyclohexylphosphino-2'-(N,N-dimethylamino)biphenyl, 1,1'-bis(diphenylphosphino)ferrocene, di-t-butylphosphonium tetrafluoroborate, and 1,3-bis(2,4,6-trimethylphenyl)imidazol-2-ylidene. A preferred example is tetrakis(triphenylphosphine)palladium(0).

The aforementioned palladium(0) catalyst can be used in an amount of 0.01 to 5 times, and preferably 0.01 to 0.1 times the molar equivalent of the compound (A-1).

The type of a base used is not particularly limited, as long as a compound of interest can be obtained and non-separable by-products are not generated. Specific examples of a base may include: inorganic bases such as tripotassium phosphate, trisodium phosphate, cesium carbonate, potassium carbonate, sodium carbonate, cesium hydrogencarbonate, potassium hydrogencarbonate, sodium hydrogencarbonate, sodium acetate, barium hydroxide, potassium hydroxide, potassium fluoride, or cesium fluoride; metal alkoxides such as sodium ethoxide or sodium-t-butoxide; acetates of alkali metals such as sodium acetate or potassium acetate; and organic bases such as triethylamine. A preferred base is sodium carbonate.

The aforementioned base can be used in an amount of 1 to 100 times, and preferably 1 to 20 times the molar equivalent of the compound (A-1).

The type of an additive used is not particularly limited, as long as a compound of interest can be obtained and non-separable by-products are not generated. Specific examples of an additive may include lithium chloride, sodium chloride, lithium bromide, sodium bromide, and tetrabutylammonium bromide.

The aforementioned additive can be used in an amount of 1 to 100 times, and preferably 1 to 10 times the molar equivalent of the compound (A-1).

The reaction temperature is not particularly limited. It is generally between −30° C. and 180° C., and preferably between 0° C. and 100° C.

The reaction time is not particularly limited. It is generally between 0.5 and 200 hours, and preferably between 1 and 100 hours.

When the reaction is carried out under the atmosphere of inert gas, the type of such inert gas is not particularly limited unless it inhibits the reaction in the present step. Specific examples may include argon or nitrogen.

<Step 2>

The present step is a step of allowing the compound (A-2) to react with methylamine in an inert solvent, so as to obtain the compound (A-3).

The aforementioned methylamine can be used in an amount of 1 to 200 times, and preferably 1 to 40 times the molar equivalent of the compound (A-2).

The type of a solvent used is not particularly limited, as long as it dissolves starting substances to a certain extent and it does not inhibit the reaction in the present step. Examples of a solvent may include: aromatic hydrocarbons such as toluene, benzene, or xylene; ethers such as diethyl ether, tetrahydrofuran, dimethoxyethane, or dioxane; alcohols such as methanol, ethanol, n-propanol, isopropanol, n-butanol, t-butanol, or ethylene glycol; water; and a mixture of these solvents. Preferred examples are isopropanol and tetrahydrofuran.

The method of adding methylamine used is not particularly limited, as long as a compound of interest can be obtained and non-separable by-products are not generated. For example, methylamine can be added in the form of gas, a solution such as methanol, ethanol, tetrahydrofuran or water, or a salt such as hydrochloride. Methylamine is preferably added as a methanol solution.

The reaction temperature is not particularly limited. It is generally between −30° C. and 180° C., and preferably between 0° C. and 150° C.

The reaction time is not particularly limited. It is generally between 0.5 and 200 hours, and preferably between 1 and 100 hours.

In the present step, in general, a hermetically sealed reactor that is resistant to pressure, such as a stainless steel reactor, is used.

The crystals of the compound (I) of the present invention can be stably produced in an industrial scale, by producing the compound (I), dissolving the above compound by heating in a specific solvent, and then cooling the obtained solution under stirring for crystallization, or recrystallizing the obtained compound.

EXAMPLES

The compound of the present invention can be produced by the methods described in the following examples. However, these examples are provided for illustrative purposes only. Specific examples as described below are not intended to limit the scope of the invention in any case. In addition, various modifications may also be made within the scope of the present invention.

Compounds, to which publication names or the like are attached, were produced in accordance with the publications or the like.

Production Example 1

Synthesis of 3-(2-chloro-6,7-dimethoxy-quinazolin-4-yl)phenylamine

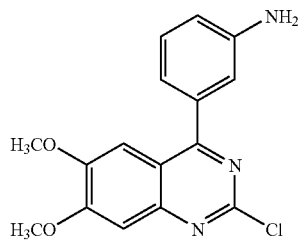

Twenty-five grams of 2,4-dichloro-6,7-dimethoxyquinazoline was suspended in 2.25 L of a mixed solution consisting of toluene:tetrahydrofuran:a 2 N sodium carbonate solution=1:1:1. To the reaction mixture was added 21.5 g of 3-aminophenyl boronic acid ½ sulfate, and the mixture was degassed, the atmosphere in the reaction vessel was replaced with nitrogen. To the reaction mixture was added 2.23 g of tetrakis(triphenylphosphine)palladium(0), followed by stirring at 60° C. under a nitrogen atmosphere. Eighteen hours after initiation of the reaction, 1.2 g of tetrakis(triphenylphosphine)palladium(0) was added to the reaction mixture, and the stirring was continued. Thirty hours later, 1.2 g of tetrakis(triphenylphosphine)palladium(0) was further added to the reaction mixture, and stirring was further continued. Forty-eight hours after initiation of the reaction, the reaction mixture was cooled, and it was then transferred into a separatory funnel, so as to separate an organic layer. The obtained organic layer was washed with 300 mL of brine, and was then dried over anhydrous magnesium sulfate. The desiccant was removed by passing it through 250 g of silica gel. The silica gel was washed with 1.5 L of ethyl acetate, and the obtained organic layers were combined and concentrated to dryness. The residue was triturated with 200 mL of ethyl acetate, and the obtained solid was then filtrated. The solid was washed with 100 mL of diethyl ether and 200 mL of a mixed solution consisting of n-heptane:ethyl acetate=1:1, and dried under aeration to yield 28.2 g of a product of interest. Yield: 92.5%

$^1$H-NMR (DMSO-d$_6$) δ (ppm): 3.86 (3H, s), 4.01 (3H, s), 5.40 (2H, br), 6.79 (1H, dd, J=1.6, 8.0 Hz), 6.93 (1H, brd, J=8.0 Hz), 7.02 (1H, t, J=1.6 Hz), 7.24 (1H, t, J=8.0 Hz), 7.41 (1H, s), 7.43 (1H, s).

Production Example 2

Synthesis of [4-(3-aminophenyl)-6,7-dimethoxyquinazolin-2-yl]methylamine

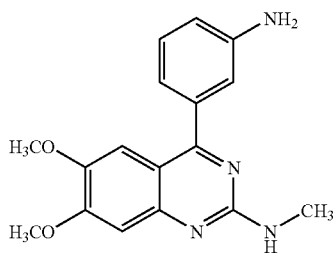

Fourteen grams of 3-(2-chloro-6,7-dimethoxyquinazolin-4-yl)phenylamine was suspended in 135 mL of a mixed solution consisting of tetrahydrofuran:isopropanol=2:1. To the reaction mixture was added 89 mL of a methylamine solution in methanol, and the reaction mixture was stirred in a pressure-resistant sealed tube reactor at 130° C. for 24 hours. After the reaction mixture was allowed to cool down to room temperature, it was diluted with 300 mL of ethyl acetate and then washed with 300 mL of water. A water layer was extracted with 100 mL of ethyl acetate, and the combined organic layer was washed with 100 mL of brine. The organic layer was separated and was then dried over anhydrous magnesium sulfate. The desiccant was removed by filtration, the organic layer was concentrated to dryness, and the resultant was triturated with a mixed solvent consisting of ethyl acetate:tetrahydrofuran=3:1. The obtained solid was filtrated, and the filtrate was then washed with ethyl acetate, and dried under aeration to yield 10 g of a product of interest. The filtrate was adsorbed on a 50 g silica gel column, and it was then eluted with a mixed solution consisting of ethyl acetate:methanol=9:1, and the eluent was concentrated to dryness. The residue was triturated with ethyl acetate, and the obtained solid was then filtrated. The solid was washed with diethyl ether, and dried under aeration to yield 1.4 g of a product of interest. Total yield: 82.9%

$^1$H-NMR (CDCl$_3$) δ (ppm): 3.12 (3H, d, J=5.2 Hz), 3.80 (2H, brs), 3.82 (3H, s), 4.03 (3H, s), 5.30 (1H, br), 6.83 (1H, dd, J=1.6, 8.0 Hz), 6.99 (1H, t, J=1.6 Hz), 7.04 (1H, brd, J=8.0 Hz), 7.07 (1H, s), 7.15 (1H, s), 7.30 (1H, t, J=8.0 Hz).

Production Example 3

Alternative Method for Synthesis of 3-(2-chloro-6,7-dimethoxy-quinazolin-4-yl)phenylamine (Production Example 1)

To 634 g of sodium carbonate (5.98 mol) was added 2.91 kg of water under a nitrogen atmosphere, followed by stirring for dissolution. To the solution were added 3.0 L of tetrahydrofuran, 431 g of 3-aminophenyl boronic acid monohydrate (2.78 mol), 30.4 g of triphenylphosphine (0.116 mol) and 26.0 g of dichloropalladium (0.116 mol) in this order. To the mixture was dropwise added a solution of 2,4-dichloro-6,7-dimethoxyquinazoline (600 g; 2.32 mol) in tetrahydrofuran (12.0 L) over 2 hours while stirring at 60° C., followed by stirring at the same temperature for 16 hours. To the mixture were added 3.0 kg of a 5% sodium chloride solution and 12.0 L of tetrahydrofuran in this order, and the mixture was stirred at 50° C. for 1 hour and allowed to cool down to 25° C. The mixture was filtered through celite to remove the insoluble matter, and the filtrate was transferred to separatory funnel and the organic layer was separated. To the separated organic layer were added 150 g of anhydrous magnesium sulfate and 60.0 g of activated carbon, and the mixture was stirred at 50° C. for 1 hour and allowed to cool down to 25° C. The mixture was filtered through celite to remove the insoluble matter, and the filtrate was concentrated under reduced pressure. To the residue was added 6.0 L of water, and the mixture was stirred at room temperature for 1 hour, and precipitated crystals were collected by filtration. The collected crystals were dried at 50° C. under reduced pressure to yield 730 g of a product of interest. Yield: 62.1%

Production Example 4

Alternative Method for Synthesis of [4-(3-aminophenyl)-6,7-dimethoxyquinazolin-2-yl]methylamine (Production Example 2)

Two hundred grams of crude 3-(2-chloro-6,7-dimethoxyquinazolin-4-yl)phenylamine (content 124 g; 0.394 mol) was suspended in a mixed solution consisting of 1.2 L of tetrahydrofuran and 0.6 L of isopropanol. To the mixture was added 1.2 L of a methylamine solution in methanol, and the mixture was stirred in a SUS autoclave at 90° C. for 15 hours. The reaction mixture was allowed to cool down to 25° C., and concentrated under reduced pressure. To the residue were added 1.0 L of water and 4.0 L of chloroform, and the mixture was stirred at 50° C. for 0.5 hours and allowed to cool down to 25° C. The mixture was filtered through celite to remove the insoluble matter, and the filtrate was transferred to separatory funnel and the organic layer was separated. To the separated organic layer were added 50.0 g of anhydrous magnesium sulfate and 20.0 g of activated carbon, and the mixture was stirred at 50° C. for 1 hour and allowed to cool down to 25° C. The mixture was filtered through celite to remove the insoluble matter, and the filtrate was concentrated under reduced pressure. To the residue was added 904 mL of chloroform, and the mixture was stirred at 50° C. for 1 hour and stirred overnight after turning off the heater. Then the mixture was stirred in an ice bath for 2 hours and precipitated crystals were collected by filtration. The collected crystals were dried at 50° C. under reduced pressure to yield 76.3 g of a product of interest. Yield: 38.7%

Example 1

Synthesis of methyl N-[3-(6,7-dimethoxy-2-methylaminoquinazolin-4-yl)phenyl]terephthalamic acid

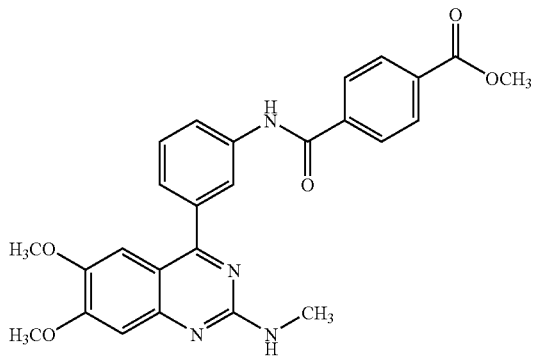

To a solution of 16.8 g of [4-(3-aminophenyl)-6,7-dimethoxyquinazolin-2-yl]methylamine and 8.6 g of pyridine dissolved in 300 mL of tetrahydrofuran was added 11.8 g of 4-chlorocarbonylbenzoic acid methyl ester at room temperature, followed by stirring for 24 hours. To the reaction mixture was added 100 mL of dimethyl sulfoxide, the mixture was partitioned between a mixed solvent consisting of 2,000 mL of ethyl acetate and 1,000 mL of tetrahydrofuran, and 1,000 mL of a saturated sodium hydrogencarbonate solution, and the organic layer was separated. The water layer was further extracted with a mixed solvent consisting of 500 mL of ethyl acetate and 500 mL of tetrahydrofuran. The combined organic layer was then washed with 1,000 mL of a saturated sodium hydrogencarbonate solution and 1,000 mL of brine in this order, and dried over anhydrous magnesium sulfate. The desiccant was removed by filtration with 100 g of a basic silica gel pad, followed by well washing with 2,000 mL of ethyl acetate. The combined eluent was concentrated under reduced pressure, and the obtained crude product was suspended and triturated in a mixed solvent consisting of 100 mL of tetrahydrofuran and 500 mL of diethyl ether. The precipitated crystals were collected by filtration, washed twice with 100 mL of diethyl ether, and dried under aeration at 50° C. for 5 hours to yield 13.8 g of the crystals of the titled compound (yield: 53.2%).

$^1$H-NMR (DMSO-d$_6$) δ (ppm): 2.88 (3H, d, J=4.4 Hz), 3.74 (3H, s), 3.89 (3H, s), 3.92 (3H, s), 6.99 (1H, s), 7.00 (1H, brs), 7.17 (1H, s), 7.46 (1H, d, J=8.0 Hz), 7.55 (1H, t, J=8.0 Hz), 7.87 (1H, brd, J=8.0 Hz), 8.08 (4H, s), 8.20 (1H, brs), 10.61 (1H, s).

Example 2

Synthesis of N-[3-(6,7-dimethoxy-2-methylamino-quinazolin-4-yl)phenyl]terephthalamic acid hydrochloride

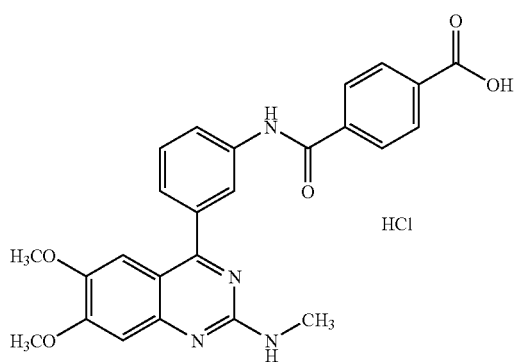

To a solution of 2.5 g of methyl N-[3-(6,7-dimethoxy-2-methylaminoquinazolin-4-yl)phenyl]terephthalamic acid dissolved in a mixed solvent consisting of 50 mL of tetrahydrofuran and 25 mL of methanol was added 11.3 mL of a 5 N sodium hydroxide solution, followed by stirring at room temperature for 12 hours. The reaction mixture was adjusted to be acidic by addition of 5 N hydrochloric acid, and the obtained solid was then filtrated, washed with 10 mL of water and 20 mL of ether, and dried under aeration to yield 2.5 g of a product of interest. Yield: 95.3%.

$^1$H-NMR (DMSO-d$_6$) δ (ppm): 3.05 (3H, brs), 3.82 (3H, s), 3.98 (3H, s), 7.32 (1H, s), 7.54 (1H, brd, J=8.0 Hz), 7.55 (1H, brs), 7.61 (1H, t, J=8.0 Hz), 7.91 (1H, d, J=8.0 Hz), 8.06 (4H, s), 8.35 (1H, brs), 10.71 (1H, s).

Example 3

Synthesis of N-[3-(6,7-dimethoxy-2-methylamino-quinazolin-4-yl)phenyl]-N',N'-dimethylterephthalamide

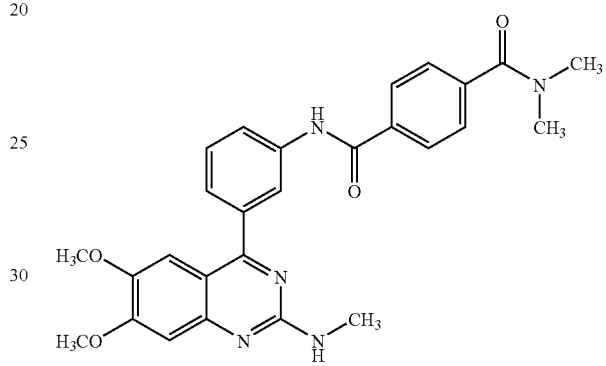

To a solution of 100 mg of N-[3-(6,7-dimethoxy-2-methylaminoquinazolin-4-yl)phenyl]terephthalamic acid hydrochloride dissolved in 2 mL of dimethylformamide were added 60 mg of WSC, 41 mg of 1-hydroxybenzotriazole, 42 μL of triethylamine, and 10 mg of 4-dimethylaminopyridine, followed by stirring at room temperature for 30 minutes. To the reaction mixture was added 200 μL of a dimethylamine solution in tetrahydrofuran, followed by stirring at room temperature for 15 hours. To the reaction mixture was added 2 mL of tetrahydrofuran, and the reaction mixture was partitioned after addition of a saturated sodium hydrogencarbonate solution. The organic layer was extracted with 10 mL of ethyl acetate, washed with brine, and dried over anhydrous magnesium sulfate. The anhydrous magnesium sulfate was removed by filtration, and the organic layer was concentrated to dryness, and the residue was triturated with a mixed solution consisting of ethyl acetate:n-heptane=1:1. The obtained solid was filtrated, washed with diethyl ether, and dried under aeration to yield 85 mg of a product of interest. Yield: 87%.

$^1$H-NMR (CD$_3$OD) δ (ppm): 3.01 (3H, s), 3.05 (3H, s), 3.13 (3H, s), 3.83 (3H, s), 3.99 (3H, s), 7.11 (1H, s), 7.27 (1H, s), 7.52 (1H, ddd, J=1.6, 1.6, 8.0 Hz), 7.57 (2H, d, J=8.4 Hz), 7.58 (1H, t, J=8.4 Hz), 7.81 (1H, ddd, J=1.6, 2.0, 8.0 Hz), 8.04 (2H, d, J=8.4 Hz), 8.19 (1H, t, J=2.0 Hz).

The following compounds of Examples 4 to 10 were synthesized by methods similar to Example 3, using the compound of Example 2 as a starting substance, and also using the corresponding alcohol or amine.

Example 4

Synthesis of ethyl N-[3-(6,7-dimethoxy-2-methylaminoquinazolin-4-yl)phenyl]terephthalamic acid

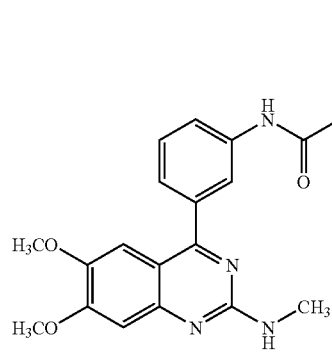

$^1$H-NMR (DMSO-$d_6$) δ (ppm): 1.33 (3H, t, J=7.2 Hz), 2.84 (3H, d, J=4.8 Hz), 3.74 (3H, s), 3.91 (3H, s), 4.34 (2H, q, J=7.2 Hz), 6.99 (1H, s), 7.00 (1H, brs), 7.17 (1H, s), 7.47 (1H, d, J=8.0 Hz), 7.55 (1H, t, J=8.0 Hz), 7.88 (1H, brd, J=8.0 Hz), 8.08 (4H, s), 8.20 (1H, brs), 10.61 (1H, s).

Example 5

Synthesis of N-[3-(6,7-dimethoxy-2-methylaminoquinazolin-4-yl)phenyl]-N'-methylterephthalamide

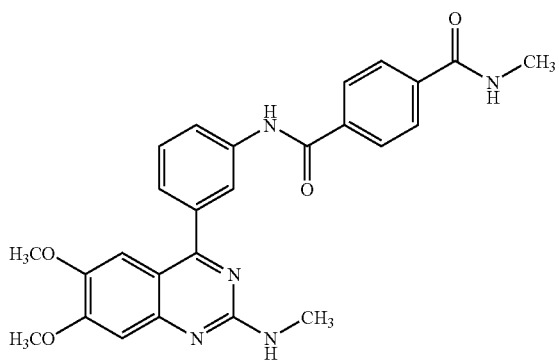

$^1$H-NMR (DMSO-$d_6$) δ (ppm): 2.81 (3H, d, J=4.4 Hz), 2.90 (3H, d, J=5.2 Hz), 3.75 (3H, s), 3.93 (3H, s), 6.99 (1H, s), 7.01 (1H, brs), 7.18 (1H, s), 7.46 (1H, d, J=8.0 Hz), 7.55 (1H, t, J=8.0 Hz), 7.89 (1H, brd, J=8.0 Hz), 7.96 (2H, d, J=8.8 Hz), 8.04 (2H, d, J=8.8 Hz), 8.21 (1H, t, J=1.6 Hz), 8.59 (1H, br), 10.53 (1H, s).

Example 6

Synthesis of propyl N-[3-(6,7-dimethoxy-2-methylaminoquinazolin-4-yl)phenyl]terephthalamic acid

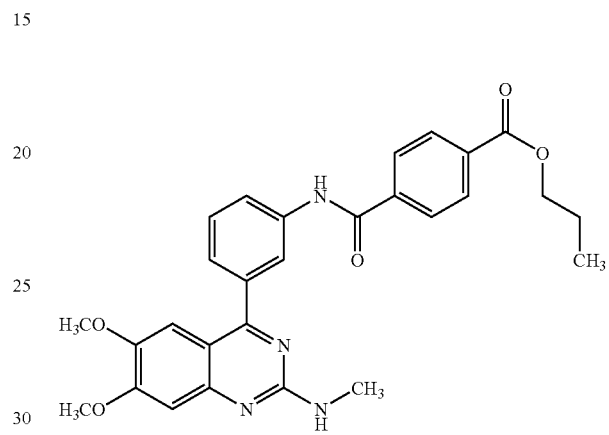

$^1$H-NMR (DMSO-$d_6$) δ (ppm): 0.99 (3H, t, J=7.6 Hz), 1.76 (2H, m), 2.90 (3H, d, J=5.2 Hz), 3.76 (3H, s), 3.93 (3H, s), 4.28 (2H, t, J=6.8 Hz), 7.01 (1H, s), 7.03 (1H, brs), 7.19 (1H, s), 7.49 (1H, d, J=8.0 Hz), 7.57 (1H, t, J=8.0 Hz), 7.90 (1H, brd, J=8.0 Hz), 8.11 (4H, s), 8.22 (1H, brs), 10.65 (1H, s).

Example 7

Synthesis of isopropyl N-[3-(6,7-dimethoxy-2-methylaminoquinazolin-4-yl)phenyl]terephthalamic acid

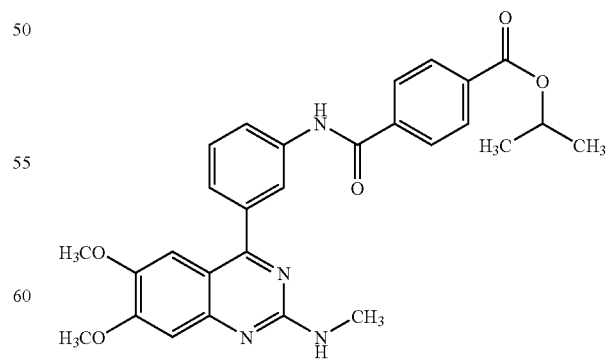

$^1$H-NMR (DMSO-$d_6$) δ (ppm): 1.35 (6H, d, J=6.4 Hz), 2.90 (3H, d, J=5.2 Hz), 3.76 (3H, s), 3.93 (3H, s), 5.18 (1H, m), 7.01 (1H, s), 7.03 (1H, brs), 7.19 (1H, s), 7.49 (1H, d, J=8.0 Hz), 7.57 (1H, t, J=8.0 Hz), 7.91 (1H, brd, J=8.0 Hz), 8.09 (4H, s), 8.22 (1H, brs), 10.65 (1H, s).

Example 8

Synthesis of N-[3-(6,7-dimethoxy-2-methylamino-quinazolin-4-yl]-N'-ethylterephthalamide

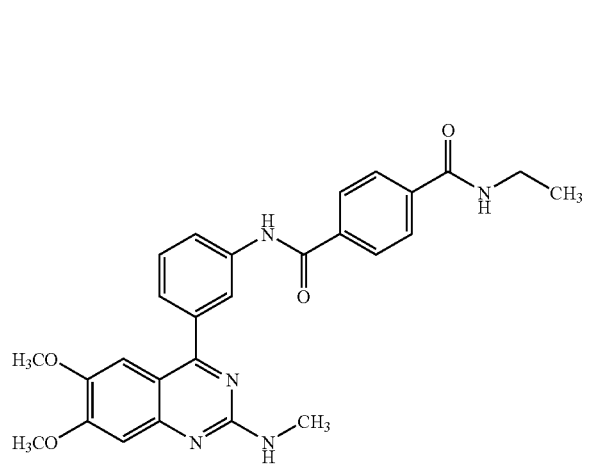

$^1$H-NMR (DMSO-d$_6$) δ (ppm): 1.15 (3H, t, J=7.2 Hz), 2.91 (3H, d, J=4.8 Hz), 3.32 (2H, m), 3.76 (3H, s), 3.94 (3H, s), 7.01 (1H, s), 7.03 (1H, brs), 7.19 (1H, s), 7.48 (1H, d, J=8.0 Hz), 7.57 (1H, t, J=8.0 Hz), 7.91 (1H, brd, J=8.0 Hz), 7.98 (2H, d, J=8.4 Hz), 8.06 (2H, d, J=8.4 Hz), 8.22 (1H, brs), 8.64 (1H, t, J=5.6 Hz), 10.55 (1H, s).

Example 9

Synthesis of N-[3-(6,7-dimethoxy-2-methylamino-quinazolin-4-yl)phenyl]-N'-propylterephthalamide

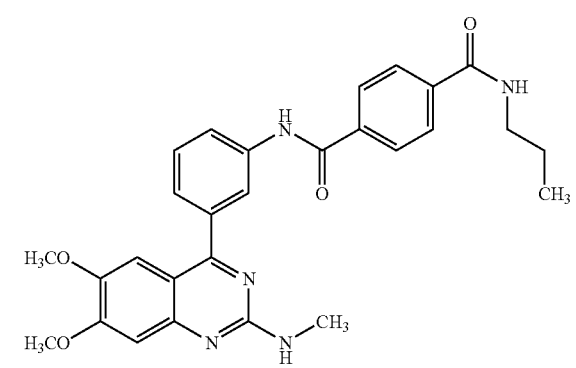

$^1$H-NMR (DMSO-d$_6$) δ (ppm): 0.91 (3H, t, J=7.6 Hz), 1.56 (2H, m), 2.91 (3H, d, J=4.8 Hz), 3.25 (2H, q, J=6.0 Hz), 3.76 (3H, s), 3.94 (3H, s), 7.01 (1H, s), 7.02 (1H, brs), 7.19 (1H, s), 7.48 (1H, d, J=8.0 Hz), 7.57 (1H, t, J=8.0 Hz), 7.91 (1H, brd, J=8.0 Hz), 7.98 (2H, d, J=8.4 Hz), 8.06 (2H, d, J=8.4 Hz), 8.22 (1H, brs), 8.62 (1H, t, J=6.0 Hz), 10.55 (1H, s).

Example 10

Synthesis of N-[3-(6,7-dimethoxy-2-methylamino-quinazolin-4-yl)phenyl]-N'-isopropylterephthalamide

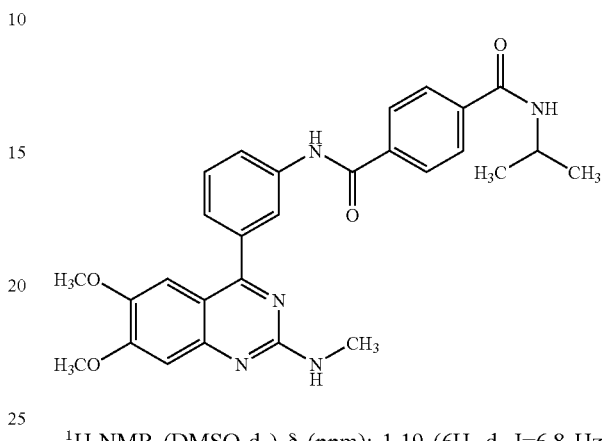

$^1$H-NMR (DMSO-d$_6$) δ (ppm): 1.19 (6H, d, J=6.8 Hz), 2.91 (3H, d, J=4.8 Hz), 3.76 (3H, s), 3.94 (3H, s), 4.12 (1H, m), 7.01 (1H, s), 7.02 (1H, brs), 7.19 (1H, s), 7.48 (1H, d, J=8.0 Hz), 7.57 (1H, t, J=8.0 Hz), 7.92 (1H, brd, J=8.0 Hz), 7.98 (2H, d, J=8.4 Hz), 8.05 (2H, d, J=8.4 Hz), 8.22 (1H, brs), 8.34 (1H, d, J=7.6 Hz), 10.55 (1H, s).

Example 11

Synthesis of methyl N-[3-(6,7-dimethoxy-2-methylaminoquinazolin-4-yl)phenyl]isophthalic acid

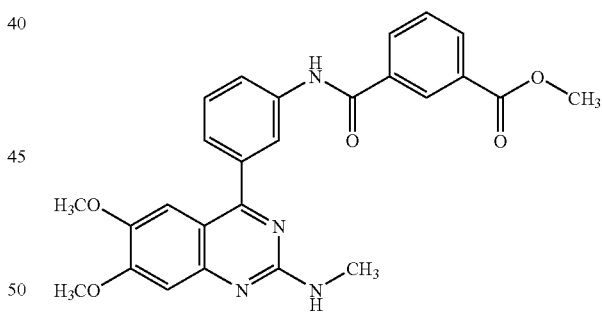

A mixture of 2.00 g (6.44 mmol) of 3-(2-chloro-6,7-dimethoxyquinazolin-4-yl)phenylamine, 1.75 g (9.71 mmol) of isophthalic acid monomethyl ester, 2.7 mL of triethylamine, 1.00 g of 1-hydroxybenzotriazole hydrate, and 2.00 g of WSC hydrochloride, was suspended in 15 mL of dimethylformamide, followed by stirring at room temperature overnight. The reaction mixture was poured into water, and extracted with ethyl acetate. The organic layer was washed with brine, and dried over magnesium sulfate. After filtration, the residue obtained by solvent distillation under reduced pressure was then subjected to silica gel column chromatography (ethyl acetate-heptane). Thereafter, a solid precipitated with ethyl acetate-hexane was collected by filtration, and dried under aeration to yield 2.65 g of the titled compound (yield: 87%).

¹H-NMR (DMSO-d₆) δ (ppm): 2.91 (3H, d, J=4.8 Hz), 3.76 (3H, s), 3.92 (3H, s), 3.93 (3H, s), 7.01 (1H, s), 7.02 (1H, brs), 7.19 (1H, s), 7.48 (1H, brd, J=8.0 Hz), 7.57 (1H, t, J=8.0 Hz), 7.72 (1H, t, J=8.0 Hz), 7.92 (1H, brd, J=8.0 Hz), 8.17 (1H, brd, J=8.0 Hz), 8.22 (1H, t, J=1.6 Hz), 8.26 (1H, brd, J=8.0 Hz), 8.56 (1H, t, J=1.6 Hz), 10.67 (1H, s).

Example 12

Synthesis of N-[3-(6,7-dimethoxy-2-methylaminoquinazolin-4-yl)phenyl]isophthalic acid

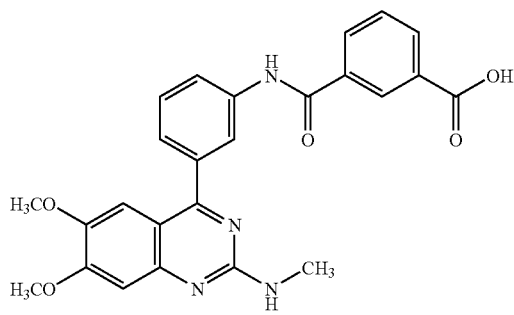

To a solution of 2.49 g (5.27 mmol) of the compound of Example 11 as obtained above dissolved in a mixed solvent consisting of 40 mL of tetrahydrofuran and 40 mL of ethanol was added 15 mL of a 1 N sodium hydroxide aqueous solution, followed by stirring at room temperature overnight. The reaction mixture was neutralized with 15 mL of 1 N hydrochloric acid, and 60 mL of water was added thereto. The precipitated solid was collected by filtration, and dried under hot air to yield 3.31 g of the titled compound.

¹H-NMR (DMSO-d₆) δ (ppm): 2.91 (3H, d, J=4.8 Hz), 3.76 (3H, s), 3.94 (3H, s), 7.01 (1H, s), 7.02 (1H, brs), 7.20 (1H, s), 7.48 (1H, brd, J=8.0 Hz), 7.57 (1H, t, J=8.0 Hz), 7.69 (1H, t, J=8.0 Hz), 7.92 (1H, brd, J=8.0 Hz), 8.15 (1H, brd, J=8.0 Hz), 8.22 (1H, brd, J=8.0 Hz), 8.23 (1H, t, J=1.6 Hz), 8.56 (1H, t, J=1.6 Hz), 10.65 (1H, s).

The following compounds of Examples 13 to 19 were synthesized by methods similar to Example 3, using the compound of the aforementioned Example 12 as a starting substance, and also using the corresponding alcohol or amine.

Example 13

Synthesis of ethyl N-[3-(6,7-dimethoxy-2-methylaminoquinazolin-4-yl)phenyl]isophthalic acid

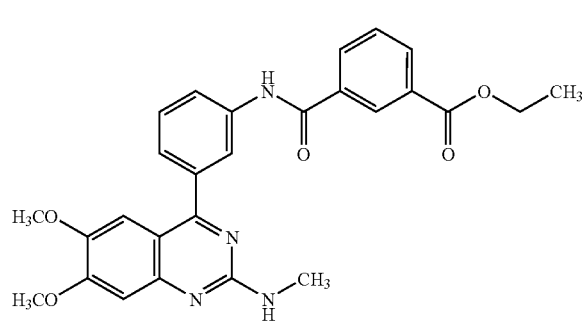

¹H-NMR (DMSO-d₆) δ (ppm): 1.36 (3H, t, J=7.2 Hz), 2.91 (3H, d, J=4.8 Hz), 3.76 (3H, s), 3.93 (3H, s), 4.38 (2H, q, J=7.2 Hz), 7.01 (1H, s), 7.02 (1H, brs), 7.19 (1H, s), 7.48 (1H, brd, J=8.0 Hz), 7.57 (1H, t, J=8.0 Hz), 7.71 (1H, t, J=8.0 Hz), 7.92 (1H, brd, J=8.0 Hz), 8.17 (1H, brd, J=8.0 Hz), 8.22 (1H, t, J=1.6 Hz), 8.25 (1H, brd, J=8.0 Hz), 8.54 (1H, t, J=1.6 Hz), 10.67 (1H, s).

Example 14

Synthesis of propyl N-[3-(6,7-dimethoxy-2-methylaminoquinazolin-4-yl)phenyl]isophthalic acid

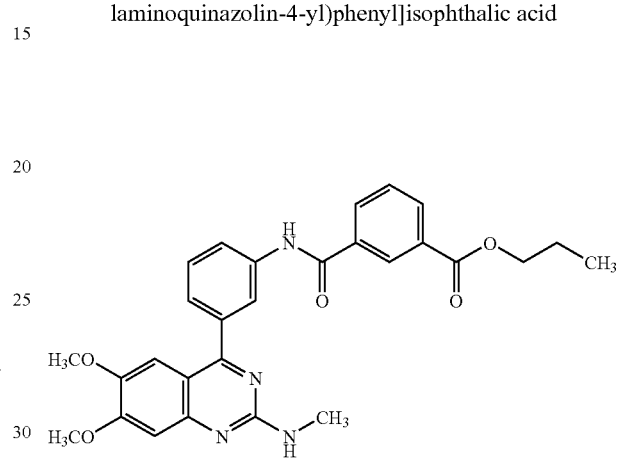

¹H-NMR (DMSO-d₆) δ (ppm): 0.99 (3H, t, J=7.2 Hz), 1.76 (2H, qt, J=7.2, 6.8 Hz), 2.91 (3H, d, J=4.4 Hz), 3.76 (3H, s), 3.93 (3H, s), 4.29 (2H, t, J=6.8 Hz), 7.01 (1H, s), 7.02 (1H, brs), 7.19 (1H, s), 7.49 (1H, brd, J=8.0 Hz), 7.57 (1H, t, J=8.0 Hz), 7.72 (1H, t, J=8.0 Hz), 7.91 (1H, brd, J=8.0 Hz), 8.18 (1H, brd, J=8.0 Hz), 8.22 (1H, t, J=1.6 Hz), 8.25 (1H, brd, J=8.0 Hz), 8.54 (1H, t, J=1.6 Hz), 10.67 (1H, s).

Example 15

Synthesis of isopropyl N-[3-(6,7-dimethoxy-2-methylaminoquinazolin-4-yl)phenyl]isophthalic acid

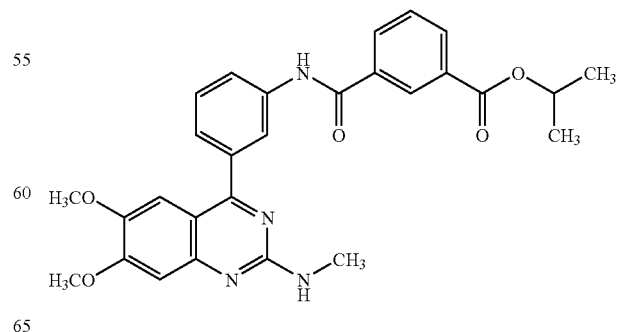

¹H-NMR (DMSO-d₆) δ (ppm): 1.36 (6H, d, J=6.4 Hz), 2.91 (3H, d, J=4.8 Hz), 3.76 (3H, s), 3.93 (3H, s), 5.19 (1H, septet, J=6.4 Hz), 7.01 (1H, s), 7.02 (1H, brs), 7.19 (1H, s), 7.48 (1H, brd, J=8.0 Hz), 7.57 (1H, t, J=8.0 Hz), 7.71 (1H, t, J=8.0 Hz), 7.91 (1H, brd, J=8.0 Hz), 8.15 (1H, brd, J=8.0 Hz), 8.21 (1H, t, J=1.6 Hz), 8.24 (1H, brd, J=8.0 Hz), 8.52 (1H, t, J=1.6 Hz), 10.67 (1H, s).

Example 16

Synthesis of N-[3-(6,7-dimethoxy-2-methylamino-quinazolin-4-yl)phenyl]-N'-methylisophthalamide

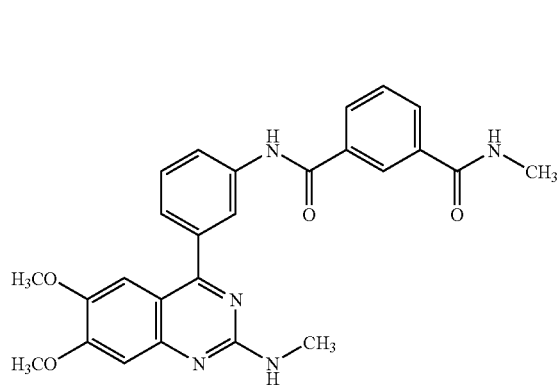

¹H-NMR (DMSO-d₆) δ (ppm): 2.82 (3H, d, J=4.4 Hz), 2.91 (3H, d, J=4.8 Hz), 3.76 (3H, s), 3.93 (3H, s), 7.01 (1H, s), 7.02 (1H, brs), 7.19 (1H, s), 7.48 (1H, brd, J=8.0 Hz), 7.57 (1H, t, J=8.0 Hz), 7.64 (1H, t, J=8.0 Hz), 7.91 (1H, brd, J=8.0 Hz), 8.02 (1H, brd, J=8.0 Hz), 8.10 (1H, brd, J=8.0 Hz), 8.22 (1H, t, J=1.6 Hz), 8.42 (1H, t, J=1.6 Hz), 8.60 (1H, brq, J=4.8 Hz), 10.58 (1H, s).

Example 17

Synthesis of N-[3-(6,7-dimethoxy-2-methylamino-quinazolin-4-yl)phenyl]-N'-ethylisophthalamide

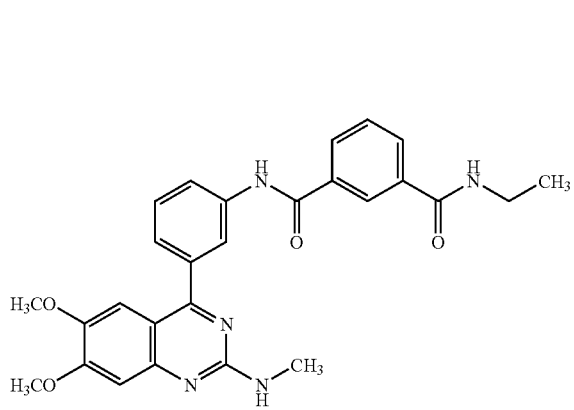

¹H-NMR (DMSO-d₆) δ (ppm): 1.15 (3H, t, J=7.2 Hz), 2.91 (3H, d, J=4.4 Hz), 3.33 (2H, q, J=7.2 Hz), 3.76 (3H, s), 3.93 (3H, s), 7.01 (1H, s), 7.02 (1H, brs), 7.19 (1H, s), 7.48 (1H, brd, J=8.0 Hz), 7.57 (1H, t, J=8.0 Hz), 7.63 (1H, t, J=8.0 Hz), 7.92 (1H, brd, J=8.0 Hz), 8.03 (1H, brd, J=8.0 Hz), 8.09 (1H, brd, J=8.0 Hz), 8.22 (1H, t, J=1.6 Hz), 8.42 (1H, t, J=1.6 Hz), 8.63 (1H, brt, J=5.4 Hz), 10.58 (1H, s).

Example 18

Synthesis of N-[3-(6,7-dimethoxy-2-methylamino-quinazolin-4-yl)phenyl]-N'-propylisophthalamide ¹H-NMR (DMSO-d₆) δ (ppm): 0.91 (3H, t, J=7.2 Hz), 1.56 (2H, qt, J=7.2, 6.4 Hz), 2.91 (3H, d, J=4.4 Hz), 3.25 (2H, dt, J=6.4, 5.4 Hz), 3.76 (3H, s), 3.93 (3H, s), 7.01 (1H, s), 7.02 (1H, brs), 7.19 (1H, s), 7.48 (1H, brd, J=8.0 Hz), 7.57 (1H, t, J=8.0 Hz), 7.63 (1H, t, J=8.0 Hz), 7.92 (1H, brd, J=8.0 Hz), 8.04 (1H, brd, J=8.0 Hz), 8.09 (1H, brd, J=8.0 Hz), 8.22 (1H, t, J=1.6 Hz), 8.42 (1H, t, J=1.6 Hz), 8.62 (1H, brt, J=5.4 Hz), 10.59 (1H, s).

Example 19

Synthesis of N-[3-(6,7-dimethoxy-2-methylamino-quinazolin-4-yl)phenyl]-N'-isopropylisophthalamide ¹H-NMR (DMSO-d₆) δ (ppm): 1.19 (6H, d, J=6.4 Hz), 2.91 (3H, d, J=4.4 Hz), 3.76 (3H, s), 3.93 (3H, s), 4.13 (1H, septet, J=6.4 Hz), 7.01 (1H, s), 7.02 (1H, brs), 7.19 (1H, s), 7.48 (1H, brd, J=8.0 Hz), 7.57 (1H, t, J=8.0 Hz), 7.62 (1H, t, J=8.0 Hz), 7.93 (1H, brd, J=8.0 Hz), 8.04 (1H, brd, J=8.0 Hz), 8.08 (1H, brd, J=8.0 Hz), 8.22 (1H, t, J=1.6 Hz), 8.40 (1H, brd), 8.41 (1H, t, J=1.6 Hz), 10.59 (1H, s).

Example 20

N-[3-(6,7-dimethoxy-2-methylaminoquinazolin-4-yl)phenyl]terephthalamic acid 2-methoxyethyl ester

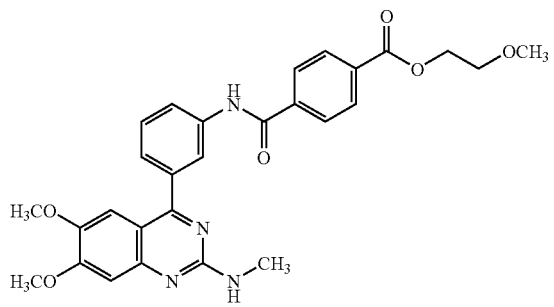

A mixture consisting of 55 mg (0.11 mmol) of N-[3-(6,7-dimethoxy-2-methylaminoquinazolin-4-yl)phenyl]terephthalamic acid hydrochloride, 40 μL (0.51 mmol) of 2-methoxyethanol, 47 μL of triethylamine, 17 mg of 1-hydroxybenzotriazole hydrate, and 35 mg of WSC hydrochloride, was suspended in 2 mL of dimethylformamide, followed by stirring at room temperature overnight. The reaction mixture was poured into water, and extracted with ethyl acetate. The organic layer was washed with brine, and was then dried over magnesium sulfate. The residue obtained by filtration and solvent distillation under reduced pressure was subjected to silica gel column chromatography (ethyl acetate-heptane). Thereafter, a solid precipitated with ethyl acetate-hexane was collected by filtration, and was dried under aeration to yield 40 mg of the titled compound (yield: 70%).

$^1$H-NMR (DMSO-$d_6$) δ (ppm): 2.91 (3H, d, J=4.8 Hz), 3.32 (3H, s), 3.69 (2H, m), 3.76 (3H, s), 3.93 (3H, s), 4.45 (2H, m), 7.01 (1H, s), 7.03 (1H, brs), 7.19 (1H, s), 7.49 (1H, brd, J=7.6 Hz), 7.57 (1H, t, J=7.6 Hz), 7.90 (1H, brd, J=7.6 Hz), 8.11 (4H, s), 8.12 (1H, t, J=1.8 Hz), 10.65 (1H, s).

Example 21

N-[3-(6,7-dimethoxy-2-methylaminoquinazolin-4-yl)phenyl]isophthalamic acid 2-methoxyethyl ester

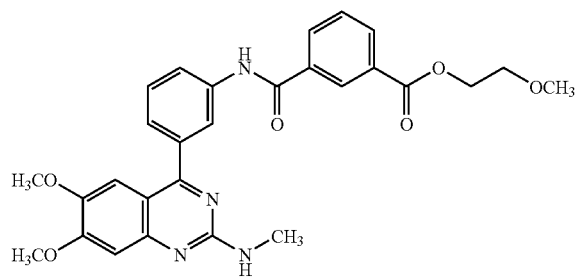

The titled compound was obtained by a method that was equivalent to a method similar to Example 3 using the compound of Example 12 as a starting substance and also using 2-methoxyethanol.

$^1$H-NMR (DMSO-$d_6$) δ (ppm): 2.91 (3H, d, J=4.8 Hz), 3.32 (3H, s), 3.69 (2H, m), 3.76 (3H, s), 3.93 (3H, s), 4.46 (2H, m), 7.01 (1H, s), 7.03 (1H, brs), 7.19 (1H, s), 7.49 (1H, brd, J=8.0 Hz), 7.57 (1H, t, J=8.0 Hz), 7.73 (1H, t, J=8.0 Hz), 7.92 (1H, brd, J=8.0 Hz), 8.17 (1H, dt, J=8.0, 1.6 Hz), 8.22 (1H, t, J=1.6 Hz), 8.26 (1H, dt, J=8.0, 1.6 Hz), 8.54 (1H, t, J=1.6 Hz), 10.68 (1H, s).

Example 22

Anhydrous Crystals 1 of methyl N-[3-(6,7-dimethoxy-2-methylaminoquinazolin-4-yl)phenyl]terephthalamic acid (Example 1)

To 75.28 mg of the compound obtained in Example 1 was added 9 mL of acetonitrile, and the mixture was heated in an oil bath for dissolution, and allowed to cool down to room temperature. The precipitate was collected by filtration, and dried at 50° C. overnight to yield the titled crystals.

Example 23

Anhydrous Crystals 2 of methyl N-[3-(6,7-dimethoxy-2-methylaminoquinazolin-4-yl)phenyl]terephthalamic acid (Example 1)

To 52.93 mg of the compound obtained in Example 1 was added 12 mL of 2-propanol, and the mixture was heated in an oil bath for dissolution, and allowed to cool down to room temperature. The precipitate was collected by filtration, and dried at 50° C. overnight to yield the titled crystals.

Example 24

Hydrate Crystals 1 of methyl N-[3-(6,7-dimethoxy-2-methylaminoquinazolin-4-yl)phenyl]terephthalamic acid (Example 1)

To 75.71 mg of the compound obtained in Example 1 was added 15 mL of acetone, and the mixture was heated in an oil bath for dissolution, and allowed to cool down to room temperature. The precipitate was collected by filtration, and dried at 50° C. overnight to yield the titled crystals.

Example 25

Hydrate Crystals 2 of methyl N-[3-(6,7-dimethoxy-2-methylaminoquinazolin-4-yl)phenyl]terephthalamic acid (Example 1)

To 75.88 mg of the compound obtained in Example 1 was added 16 mL of methanol, and the mixture was heated in an oil bath for dissolution, and allowed to cool down to room temperature. The precipitate was collected by filtration, and dried at 50° C. overnight to yield the titled crystals.

Example 26

Hydrate Crystals 3 of methyl N-[3-(6,7-dimethoxy-2-methylaminoquinazolin-4-yl)phenyl]terephthalamic acid (Example 1)

To 49.90 mg of the compound obtained in Example 1 was added 2 mL of tetrahydrofuran, and the mixture was heated in an oil bath for dissolution, and allowed to cool down to room temperature. Thereafter, 10 mL of water was further added to the mixture, which was allowed to stand. The precipitate was collected by filtration, and dried at 50° C. overnight to yield the titled crystals.

Example 27

Amorphous methyl N-[3-(6,7-dimethoxy-2-methylaminoquinazolin-4-yl)phenyl]terephthalamic acid (Example 1)

To 36.49 mg of the compound obtained in Example 1 was added 0.2 mL of dimethyl sulfoxide to dissolve the compound. Thereafter, 10 mL of water was further added to the mixture, which was allowed to stand. The precipitate was collected by filtration, and dried at 50° C. overnight to yield the titled amorphous substance.

Example 28

Alternative Method for Producing Anhydrous Crystals 1 of methyl N-[3-(6,7-dimethoxy-2-methylaminoquinazolin-4-yl)phenyl]terephthalamic acid (Example 1)

A suspension consisting of 10.00 g (55.51 mmol) of monomethyl terephthalate and 90 mL of 1,2-dimethoxyethane was stirred, while it is cooled in a cold bath at 10° C. To the suspension were added 2.0 mL of N,N-dimethylformamide and 6.61 g (52.75 mmol) of thionyl chloride in this order. The suspension was stirred under heating at 60° C. to 65° C. for 1 hour, and allowed to cool. Thereafter, the suspension was further stirred while it was cooled in an ice bath. Subsequently, 6.83 g (52.82 mmol) of diisopropylethylamine was added dropwise to the mixture. Subsequently, the reaction mixture was stirred at room temperature. Thirty minutes after the internal temperature had reached 20° C., stirring was terminated. The reaction mixture was placed in a 200-mL eggplant flask, followed by measurement to yield 109.49 g of a mixed solution consisting of [monomethyl terephthalate chloride/diisopropylethylamine] (the content of monomethyl terephthalate chloride: 8.89 g) as a slight tannish solution.

Subsequently, a suspension consisting of 9.50 g (30.00 mmol) of [4-(3-aminophenyl)-6,7-dimethoxyquinazolin-2-yl]methylamine and 380 mL of tetrahydrofuran was stirred, while it was cooled at 0° C. To the suspension was added dropwise over 1 hour, 80.71 g of the above mixed solution consisting of [monomethyl terephthalate chloride/diisopropylethylamine] (the content of monomethyl terephthalate chloride: 6.55 g; 33.00 mmol). The mixture was then stirred at 0° C. for 11 hours. Thereafter, 190 mL of ethyl acetate was added to the reaction mixture while cooling at 0° C., and 380 g of a 5% sodium hydrogencarbonate solution was then added dropwise thereto. The reaction mixture was transferred into a separatory funnel, and 190 mL of ethyl acetate was added. After extraction, the organic layer was separated, and washed with 190 g of a 5% sodium chloride solution and 190 mL of water (twice) in this order. The organic layer was concentrated under reduced pressure at 40° C. To the residue was added 143 mL of methanol, and the mixture was stirred while heating to 40° C. Thirty-three minutes after initiation of stirring, the temperature of an oil bath was set at 75° C. Thereafter, 30 minutes after the internal temperature had exceeded 60° C., the temperature of the oil bath was set at 50° C. When the internal temperature was decreased to 55° C., 143 mL of 2-propanol was added dropwise thereto. Subsequently, the internal temperature was gradually cooled to 27.3° C., and the mixture was then stirred at 20° C. for 17 hours. The precipitated crystals were subjected to vacuum filtration, and the resultant was washed with a mixed solution consisting of 14.3 mL of methanol and 14.3 mL of 2-propanol. The resultant was aspirated with a vacuum line for 10 minutes for deliquoring to yield 15.72 g of a crude product of interest (wet body; the content of a product of interest: 13.31 g) as pale yellow crystals (yield: 93.9%).

A suspension consisting of 15.48 g of the crude product of interest (wet body) (the content of the product of interest: 13.11 g; 27.00 mmol) and 40 mL of dimethyl sulfoxide was stirred under heating at 60° C., and the crystals were dissolved. The obtained solution was subjected to clarifying filtration, and washed with 10 mL of dimethyl sulfoxide. The filtrate was transferred into a 1,000-mL four-necked glass vessel, which had previously been heated with a 60° C. hot water jacket, and the residue was washed with 10 mL of dimethyl sulfoxide. The mixture was then stirred under heating at 60° C. Thereafter, 119 mL of 2-propanol was added dropwise to this solution, and 49.3 mg of seed crystals of the product of interest was placed in the mixture. Thereafter, 60 mL of 2-propanol was further added dropwise to the mixture. This suspension was stirred at 60° C. for 2 hours, the temperature of the jacket was set at 80° C., and the suspension was continuously stirred under heating for 16.5 hours. Subsequently, 120 mL of 2-propanol was added dropwise to the suspension, and 3 hours later, 362 mL of 2-propanol was further added dropwise thereto. Thereafter, the mixture was gradually cooled to 20° C. (10° C./h), and it was then stirred at the same temperature. Fifty nine point five hours later, the precipitated crystals were collected by filtration, and the crystals were washed with a mixed solution consisting of 2.6 mL of dimethyl sulfoxide and 24 mL of 2-propanol. The crystals were further washed with 40 mL of 2-propanol, and were then aspirated with a vacuum line for deliquoring. The obtained crystals were dried under reduced pressure to yield 9.84 g of a product of interest as yellow crystals (yield: 73.7%).

In order to confirm the effect of the compound of the present invention as an antipruritic agent, the present inventors have conducted the following test.

Test Example 1

Evaluation of Compounds in Oxazolone-induced Scratching Behavior Model

<Test Method>

As test animals, commercially available 5-week-old NC/Nga female mice (Japan SLC, Inc. and CRJ, Inc.) were used. For acclimation, the mice passed a preliminary breeding period of 7 days. Thereafter, only animals, wherein no changes were found in a general state and the body weight was favorably increased, were used for the test.

(1) Sensitization and Induction

Sensitization was carried out by applying once 20 μL of an acetone solution (Wako Pure Chemical Industries, Ltd.) that contained 0.5% 4-ethoxymethylene-2-phenyl-2-oxazolin-5-one (hereinafter abbreviated as "oxazolone"; Sigma) to each of the left and right pinnas of 6-week-old mice, which had passed an acclimation period.

Induction was carried out by applying 10 μL of 0.3% oxazolone to the left pinna of each mouse, 3 times in total, at intervals of 2-3 days from the 5th day after sensitization.

(2) Measurement of Scratching Behavior

For objective evaluation, the scratching behavior of each mouse was automatically measured using a Micro Act device (NeuroScience, Inc.). A magnet piece (diameter: 1 mm; length: 3 mm; NeuroScience) was inserted into the skin of the left hind-leg of each mouse anesthetized with diethyl ether (Wako Pure Chemical Industries, Ltd.) by the day before the measurement at the latest. Immediately after scratching behavior had been induced by application of oxazolone, the mouse was transferred into a chamber (diameter: 11 cm; height: 18 cm) with a coil. Thereafter, electric current induced by the movement of the magnet inserted into the leg of the mouse was measured for a certain period of time. A characteristic wave form that reflects such scratching behavior was detected by the Micro Act device, and the appearance frequency of the detected wave form was counted as a number of scratching behaviors.

(3) Evaluation of Test Substances

Preparation of test substances: The compounds of Examples 1, 4, 5, 7, 14, 20 and 21 were prepared, such that they had a concentration of 0.1-0.3% based on the concentration of a mixed solvent (acetone:ethanol=1:1).

With regard to the groups of test substances, the following 5 groups were determined: (1) normal group—a mixed solvent (acetone:ethanol=1:1) application group; (2) control group—a mixed solvent (acetone:ethanol=1:1) application group; (3) a compound of Example 1 application group; (4) a compound of Example 4 application group; and (5) a compound of Example 5 application group. In addition, the following 5 groups were determined: (1) normal group—a mixed solvent (acetone:ethanol=1:1) application group; (2) control group—a mixed solvent (acetone:ethanol=1:1) application group; (3) a compound of Example 7 application group; (4) a compound of Example 14 application group; and (5) a compound of Example 21 application group. Furthermore, the following 3 groups were determined: (1) normal group—a mixed solvent (acetone:ethanol=1:1) application group; (2) control group—a mixed solvent (acetone:ethanol=1:1) application group; and (3) a compound of Example 20 application group. The mice were divided into each group, such that the number of scratching behaviors became uniform based on the number of scratching behaviors obtained during the 2nd induction.

Evaluation of test substance: Ten microliters of a test substance (only the mixed solvent (acetone:ethanol=1:1) was applied to the normal group and the control group) was administered 1 hour before the 3rd application of oxazolone. Evaluation of the test substance was carried out, using, as an indicator, the number of scratching behaviors obtained during 2 hours after induction due to the 3rd application of oxazolone (the mixed solvent (acetone:ethanol=1:1) was applied to the normal group). In addition, another evaluation was carried out based on cutaneous symptom. That is to say, with regard to findings of scratching behaviors obtained before the 3rd application of oxazolone and 1 day or 4 days after the application, namely, with regard to each of the items of (1) abrasion and (2) bleeding/erosion, 4 stages of rating ranging from 0 to 3 (0: no symptoms; 1: slight; 2: moderate; and 3: serious) was carried out. Thus, using the difference in scores obtained before and after induction with oxazolone as an indicator, the scratching behavior was evaluated. Such rating was carried out for every item, and the total score was defined as the score of each individual.

Figure 9:
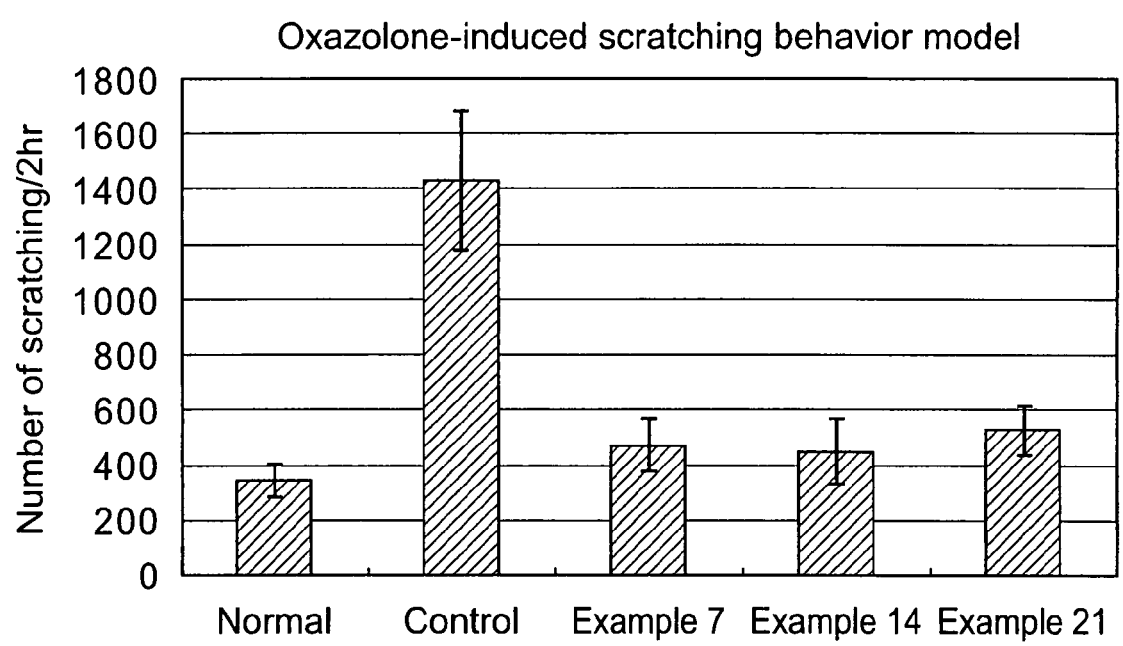
FIG. 9 shows the numbers of scratching behaviors of oxazolone-induced mice (Examples 7, 14 and 21).
Figure 11:
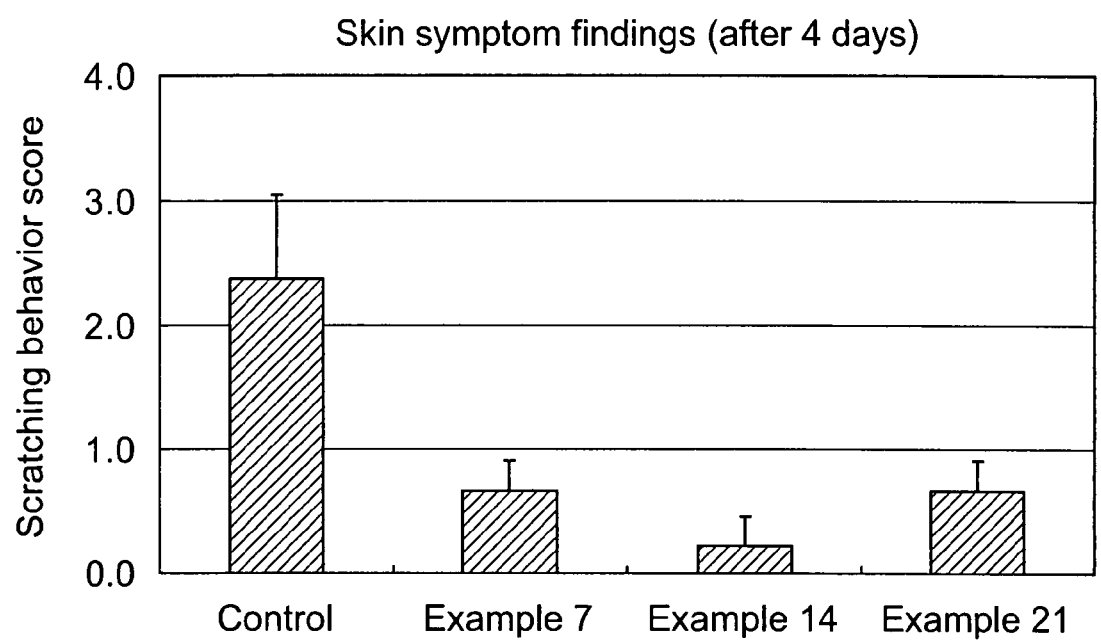
FIG. 11 shows the results of skin symptom findings (after 4 days) of oxazolone-induced mice (Example 7, 14 and 21).
Figure 12:
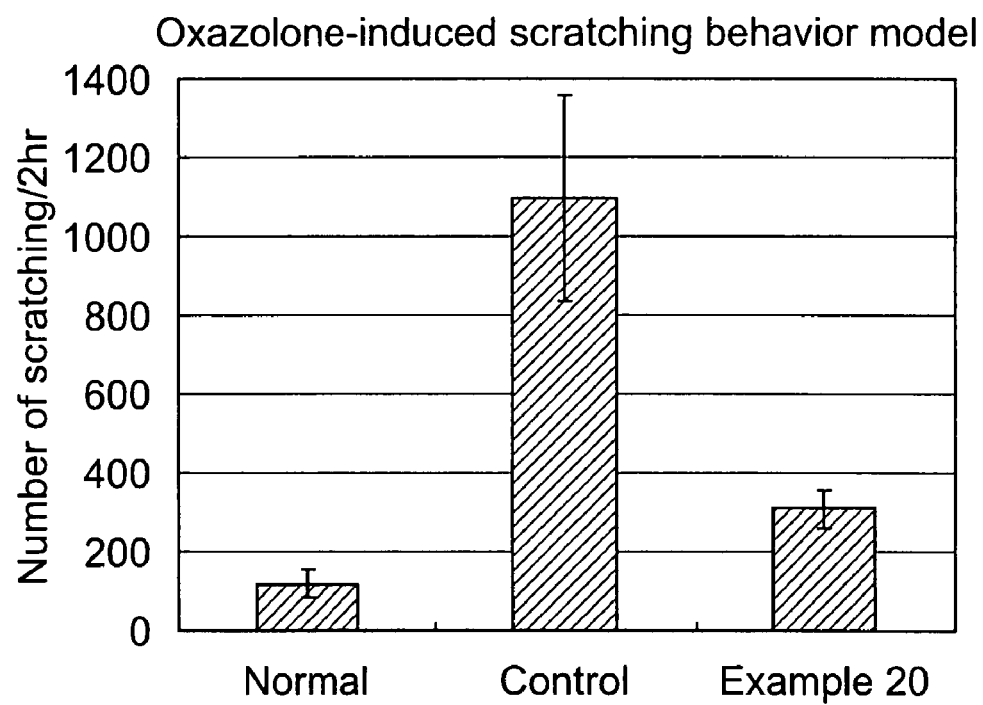
FIG. 12 shows the numbers of scratching behaviors of oxazolone-induced mice (Examples 20).

<Test Results>
(1) The measurement results regarding the number of scratching behaviors are shown in FIGS. 1, 9 and 12 (normal group: n=11; the other groups: n=17 in FIG. 1; each group: n=10 in FIGS. 9 and 12).
(2) The measurement results regarding cutaneous symptoms are shown in FIGS. 2, 10, 11, 13 and 14.

Figure 2:
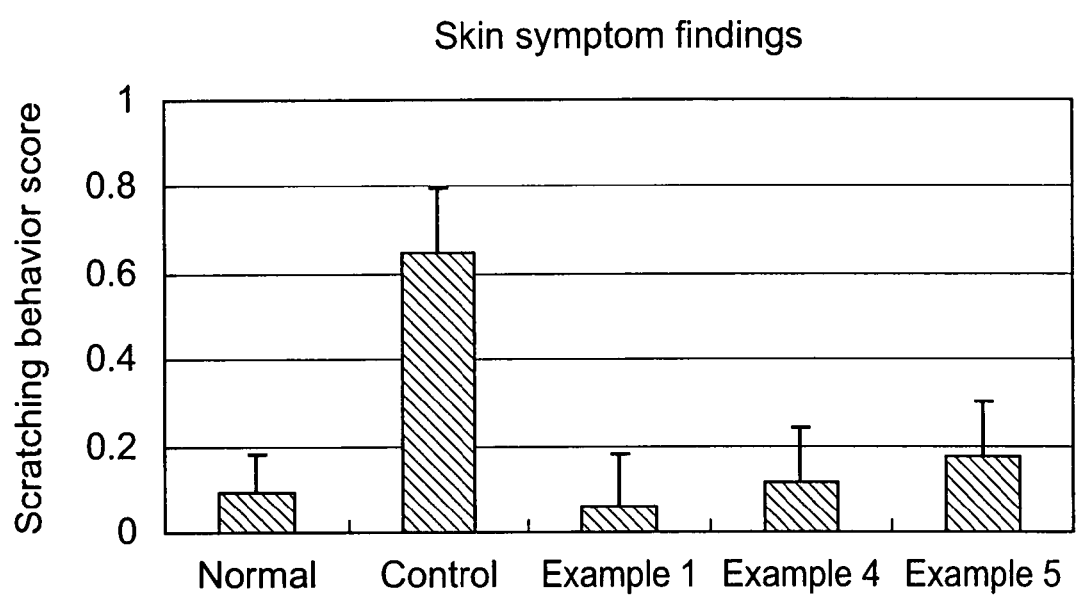
FIG. 2 shows the results of skin symptom findings (after 1 day) of oxazolone-induced mice (Example 1, 4 and 5).
Figure 3:
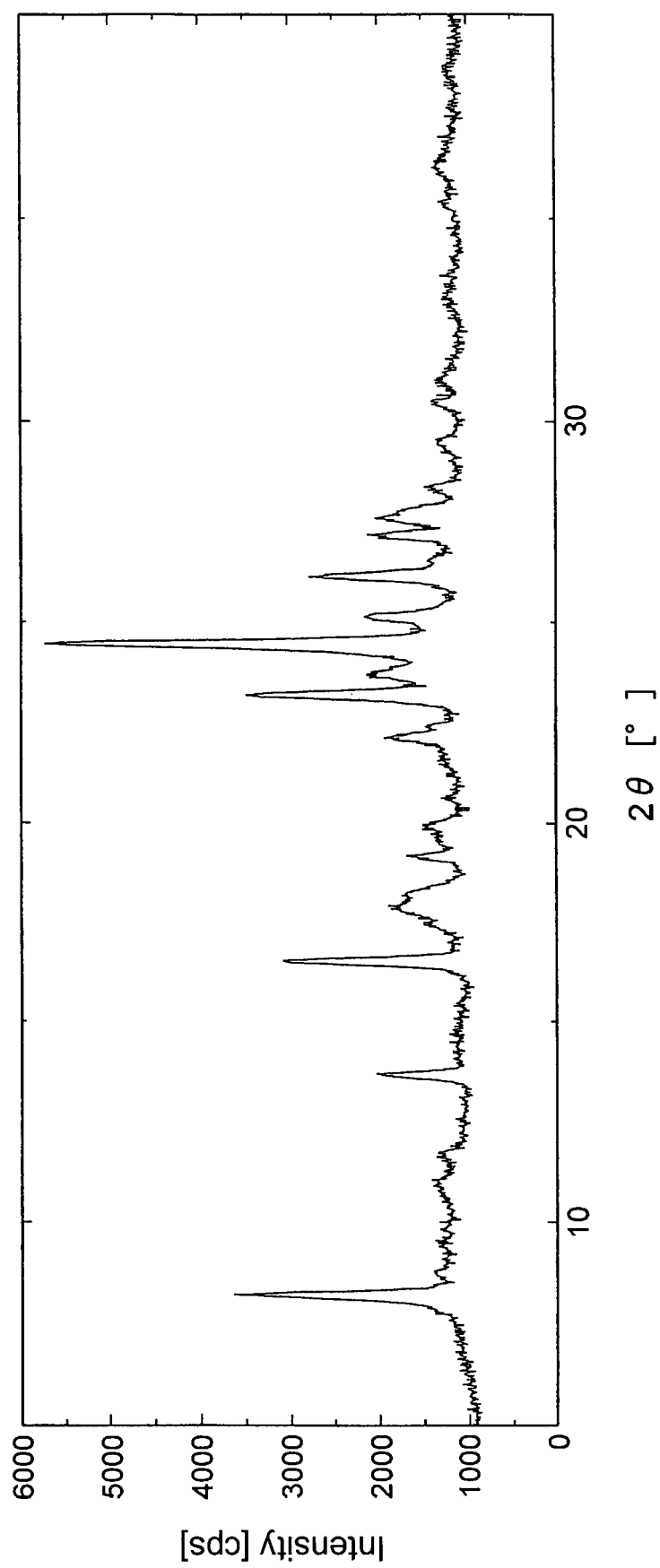
FIG. 3 shows the powder X-ray diffraction pattern of crystals obtained in Example 22.
Figure 4:
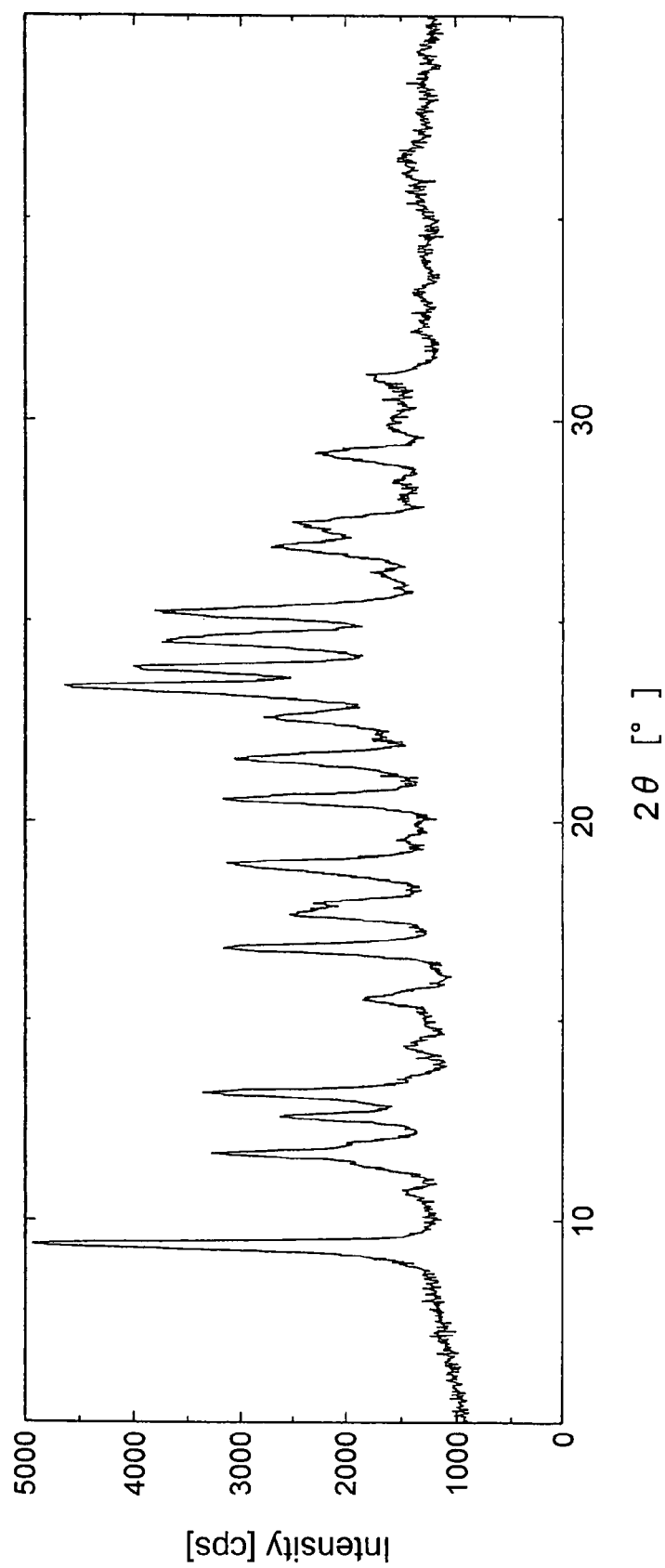
FIG. 4 shows the powder X-ray diffraction pattern of crystals obtained in Example 23.
Figure 5:
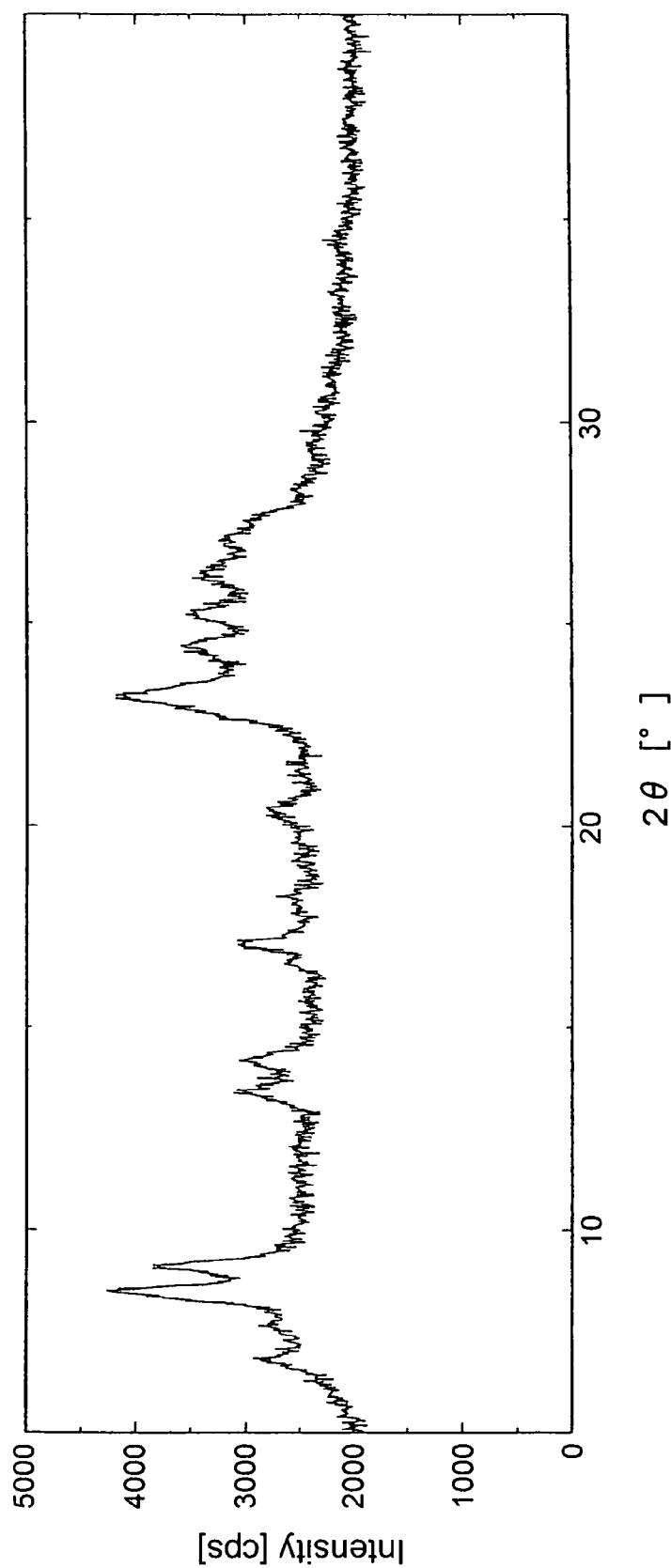
FIG. 5 shows the powder X-ray diffraction pattern of crystals obtained in Example 24.
Figure 6:
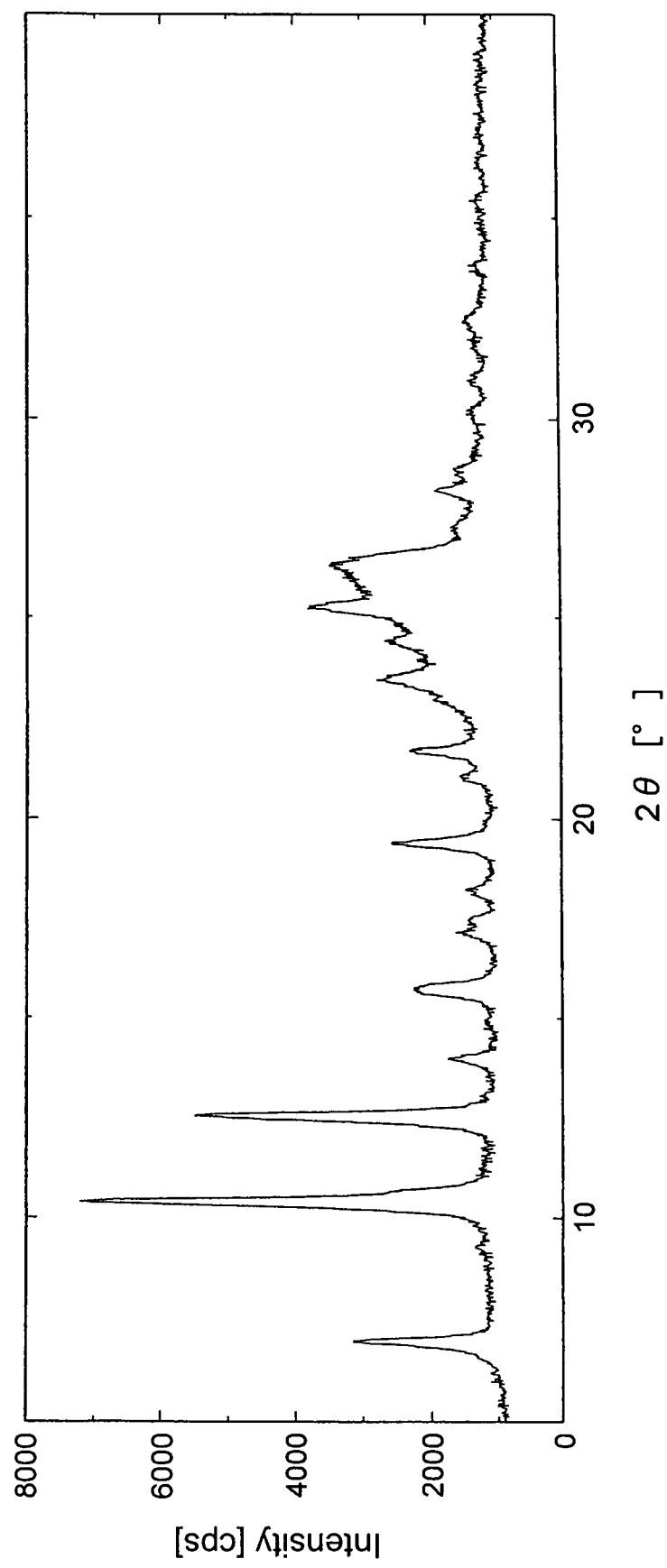
FIG. 6 shows the powder X-ray diffraction pattern of crystals obtained in Example 25.
Figure 7:
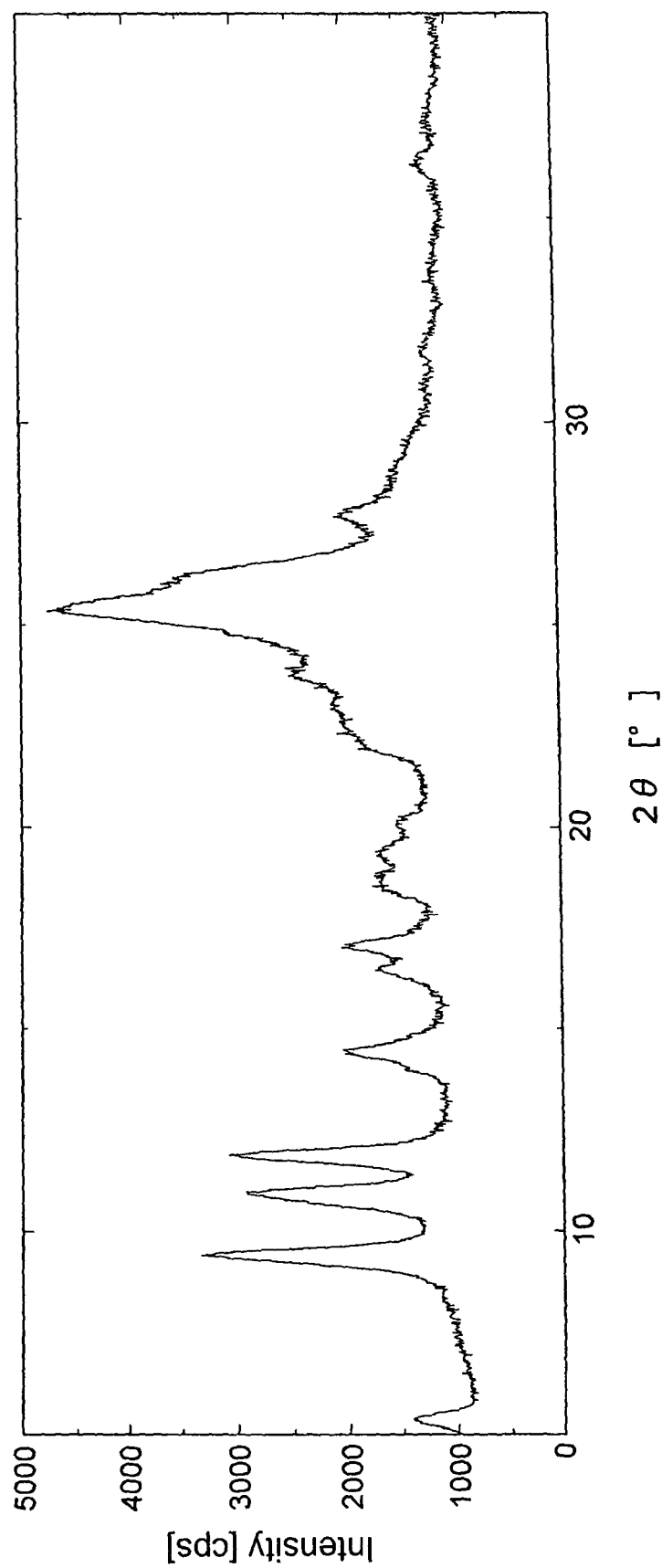
FIG. 7 shows the powder X-ray diffraction pattern of crystals obtained in Example 26.
Figure 8:
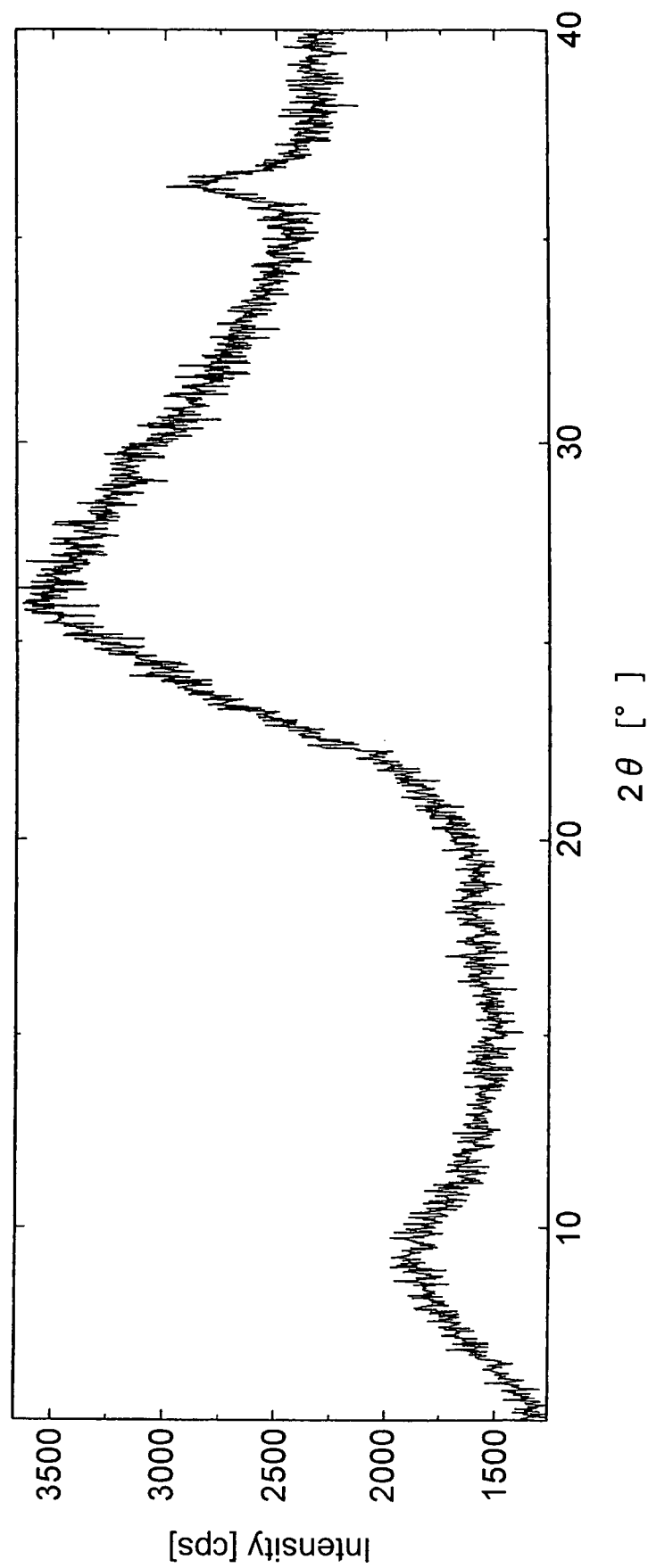
FIG. 8 shows the powder X-ray diffraction pattern of crystals obtained in Example 27.
Figure 10:
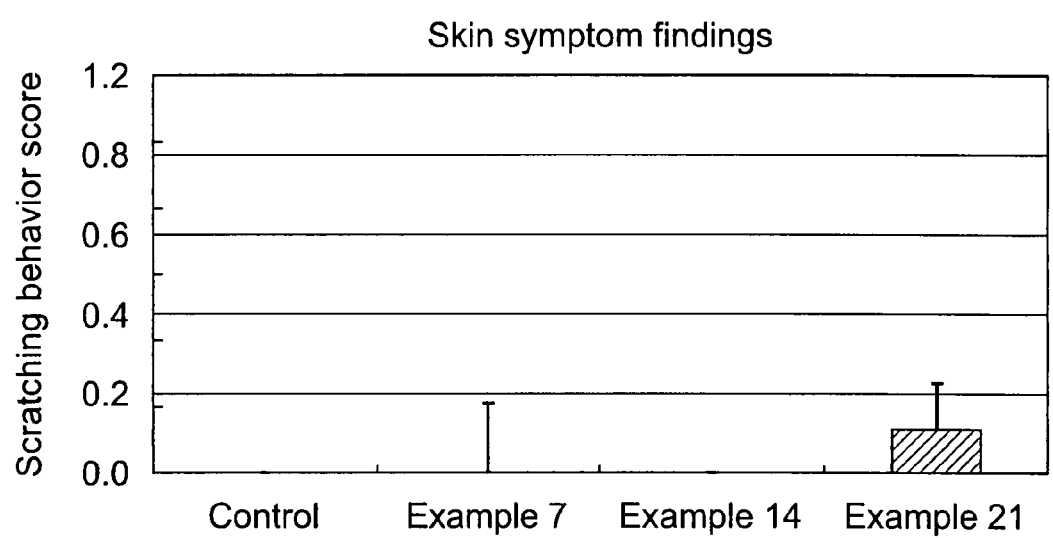
FIG. 10 shows the results of skin symptom findings (after 1 day) of oxazolone-induced mice (Example 7, 14 and 21).
Figure 13:
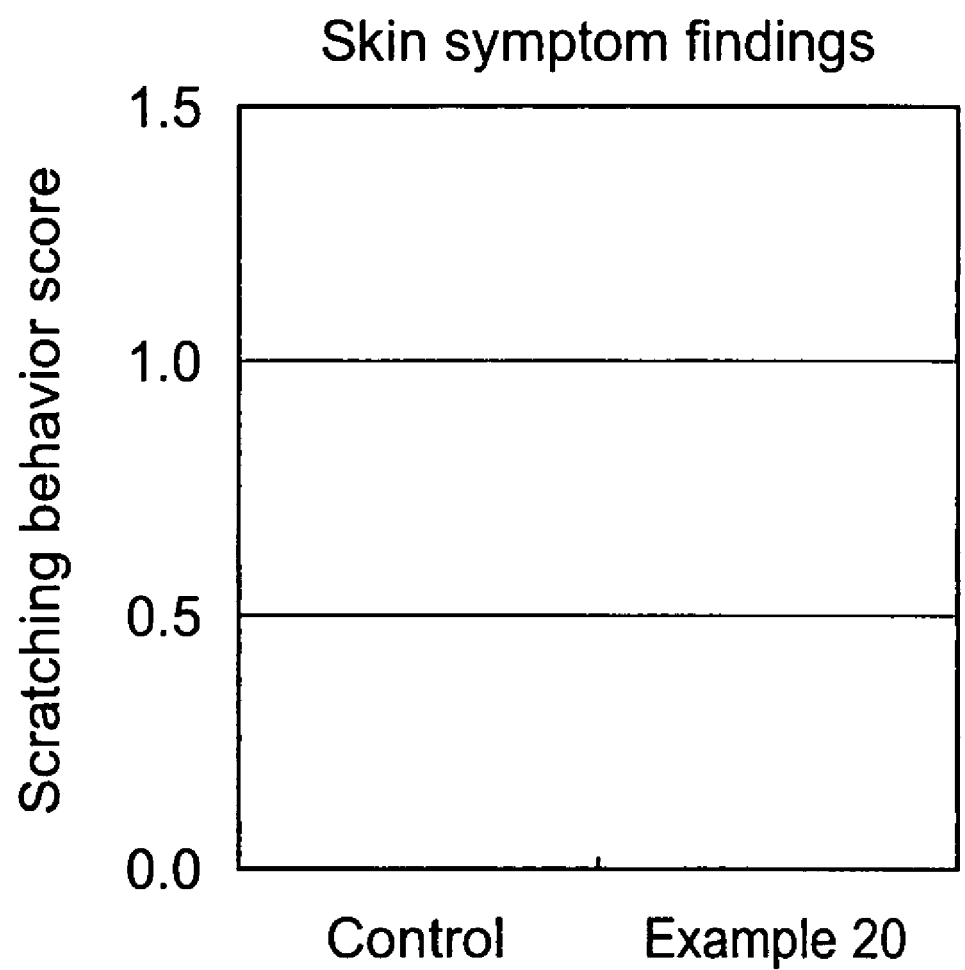
FIG. 13 shows the results of skin symptom findings (after 1 day) of oxazolone-induced mice (Example 20).
Figure 14:
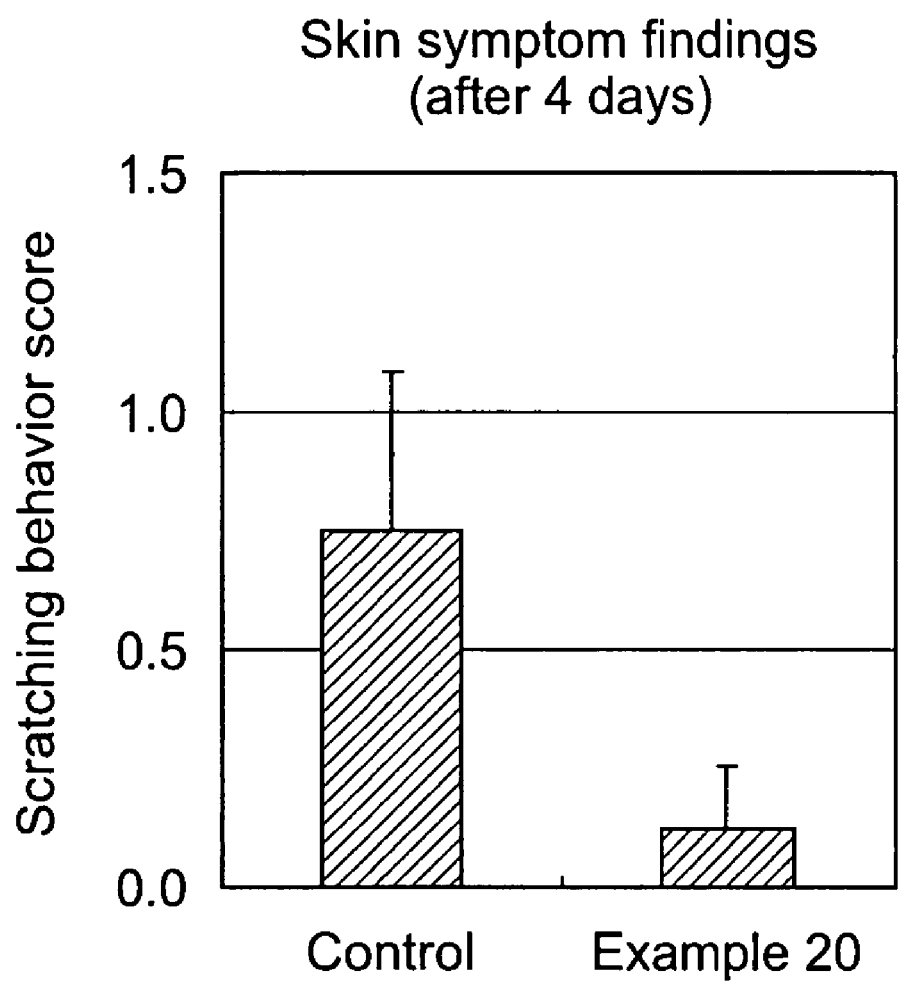
FIG. 14 shows the results of skin symptom findings (after 4 days) of oxazolone-induced mice (Example 20).

FIGS. 2, 10 and 13 are graphs made based on the value obtained by subtracting the score obtained before administration from the score obtained 1 day after administration, and FIGS. 11 and 14 are graphs made based on the value obtained by subtracting the score obtained before administration from the score obtained 4 day after administration (normal group: n=11; the other groups: n=17 in FIG. 2; normal group: n=8; the other groups: n=9 in FIGS. 10 and 11; each group: n=8 in FIGS. 13 and 14).

From these results, it was found that the compounds of the present invention suppress scratching behavior and also suppresses deterioration in cutaneous symptoms caused by such scratching behavior, thereby having an excellent antipruritic effect.

Test Example 2

Experiment to Evaluate Induction Potency of Drug Metabolizing Enzyme (CYP) using Cryopreserved Human Hepatocytes <Test Operations>

Cryopreserved human hepatocytes (XenoTeck) were rapidly thawed at 37° C., and viable cells were obtained using Hepatocytes Isolation Kit (Nosan Corporation). After cells prepared were diluted with ice cold William's Medium E (10% FBS, +PSG) to give a concentration of $5 \times 10^5$ viable cells/mL, the cells were seeded onto a 48-well collagen-coated plate (BD Biosciences) at a concentration of $1 \times 10^5$ cells/cm$^2$ and cultured at 37° C. in 5% $CO_2$ for 24 hours. Then, the medium was replaced with Hepato-STIM (registered trade mark: BD Biosciences) (+EGF, PSG, −FBS), and the cells were further cultured at 37° C. in 5% $CO_2$ for 24 hours. Hepato-STIM(+EGF, PSG, −FBS) was used as culture medium, and the cells were incubated with culture medium containing test compound, β-naphthoflavone (hereinafter abbreviated as β-NF, SIGMA) used as a positive control of human CYP1A, or rifampicin (hereinafter abbreviated as Rif, Wako Pure Chemical Industries, Ltd.) used as a positive control of human CYP3A4 at 37° C. in 5% $CO_2$ for approximately 48 hours. The culture medium containing test compound, β-NF or Rif was replaced every 24 hours. Test compound, β-NF and Rif were each dissolved in dimethyl sulfoxide (DMSO: Wako Pure Chemical Industries, Ltd.), and culture medium containing test compound (final concentrations; 1, 3 and 10 μM), β-NF (final concentration; 10 μM) or Rif (final concentration; 10 μM) was prepared by adding them to Hepato-STIM(+EGF, PSG, −FBS), respectively. Final concentration of DMSO was set to be 0.1%, and culture medium containing 0.1% DMSO was used for control. After completion of the treatment, the cells were washed with PBS once, and total RNA was purified using Total RNA Purification Kit (Applied Biosystems). The purified total RNA was subjected to reverse transcription reaction using TaqMan Reverse Transcription Reagents (Applied Biosystems) to synthesize cDNA, where oligo dT was used as a primer. The reaction was carried out using GeneAmp PCR system 9700 at 25° C. for 10 minutes, followed by at 48° C. for 60 minutes. Then, reverse transcriptase was deactivated at 95° C. for 10 minutes. The levels of mRNA for CYP1A1 and GAPDH were quantified using SYBR Green PCR Core Reagents Kit (Applied Biosystems), and those for CYP1A2 and that of CYP3A4 were measured using Taqman PCR Core Reagents Kit (Applied Biosystems) and ABI Prism 7900 Sequence Detection System (Applied Biosystems). Primer sequences and PCR conditions used for quantification of each mRNA are shown in Tables 1 and 2, respectively.

Primer Sequences

TABLE 1

| Target | Name | Sequence |
|---|---|---|
| CYP1A1 | hCYP1A1_F1 | tggtctcccttctctacactcttgt (SEQ ID NO: 1) |
| | hCYP1A1_R1 | attttccctattacattaaatcaatg gttct (SEQ ID NO: 2) |
| CYP1A2 | hCYP1A2_F_EJCP | gttcctgcagaaaacagtcca (SEQ ID NO: 3) |
| | hCYP1A2_R_EJCP | ctgtgcttgaacagggcac (SEQ ID NO: 4) |
| | hCYP1A2_probe_EJCP | agcactatcaggactttgacaagaac agtgtct (SEQ ID NO: 5) |
| CYP3A4 | hCYP3A4_F_m | gcaggaggaaattgatgcagtt (SEQ ID NO: 6) |
| | hCYP3A4_R_x | gtcaagatactccatctgtagcaca gt (SEQ ID NO: 7) |
| | hCYP3A4_probe_m | Acccaataaggcaccacccacctat ga (SEQ ID NO: 8) |
| GAPDH | hGAPDH_F | gaaggtgaaggtcggagtc (SEQ ID NO: 9) |
| | hGAPDH_R | gaagatggtgatgggatttc (SEQ ID NO: 10) |

PCR Conditions

TABLE 2

| Temperature | Time | |
|---|---|---|
| 95 | 10 min | |
| 94 | 15 sec | Denaturation |
| 58 | 20 sec | Annealing |
| 72 | 30 sec | Elongation reaction |

* A cycle consisting of denaturation, annealing, and elongation reaction, was repeated 50 times.

<Calculation of Ability to Induce CYP>

The ability of a test compound to induce CYP1A1 was calculated as follows:

Ability of a test compound to induce CYP1A1 (%)={
[(amount of mRNA of CYP1A1 in test compound treated cells)/(amount of mRNA of GAPDH in test compound treated cells)]/
[(amount of mRNA of CYP1A1 in control cells)/(amount of mRNA of GAPDH in control cells)]−1}/{[(amount of mRNA of CYP1A1 in positive control treated cells)/(amount of mRNA of GAPDH in positive control treated cells)]/
[(amount of mRNA of CYP1A1 in control cells)/(amount of mRNA of GAPDH in control cells)]−1}×100

The ability to induce CYP1A2 or CYP3A4 was calculated in the same manner described above.

<Test Results>

The results regarding the compounds of Examples 1, 4, 5, 7, 14, 16, 20, and 21 are shown in Table 3. As a comparative example, the compound described as Example 1 in WO99/37622 (4-(3-benzoylaminophenyl)-6,7-dimethoxy-2-methylaminoquinalozine) was used.

The results indicated that the compounds of the present invention do not show any induction potency on CYPs, whereas the induction potency on CYPs was observed in the comparative example.

TABLE 3

| | | Induction Ability compared to positive control (%) | | |
|---|---|---|---|---|
| | | CYP1A1 | CYP1A2 | CYP3A4 |
| Rifampicin | 10 μM | | | 100.0 |
| β-naphthoflavone | 10 μM | 100.0 | 100.0 | |
| Example 1 | 1 μM | 0.1 | −0.1 | −2.4 |
| | 3 μM | 0.6 | −0.7 | −3.4 |
| | 10 μM | 4.6 | 2.5 | −4.0 |
| Example 4 | 1 μM | 0.1 | −1.1 | −5.6 |
| | 3 μM | 0.4 | 0.6 | −6.1 |
| | 10 μM | 1.5 | 6.1 | 0.1 |
| Example 5 | 1 μM | 0.0 | −2.0 | −6.9 |
| | 3 μM | 0.0 | −1.3 | −6.2 |
| | 10 μM | 0.0 | 0.5 | −2.0 |
| Example 7 | 1 μM | 0.2 | 0.5 | −6.6 |
| | 3 μM | 1.8 | 1.5 | −9.8 |
| | 10 μM | 5.7 | 3.1 | −11.9 |
| Example 14 | 1 μM | 0.2 | 1.2 | 0.7 |
| | 3 μM | 0.3 | 3.0 | −0.1 |
| | 10 μM | 0.7 | 1.8 | −1.5 |
| Example 16 | 1 μM | 0.0 | 0.2 | −0.7 |
| | 3 μM | 0.3 | 3.9 | −0.3 |
| | 10 μM | 1.0 | 1.2 | 2.7 |
| Example 20 | 1 μM | 0.1 | −1.7 | −2.0 |
| | 3 μM | 0.1 | −1.6 | −2.1 |
| | 10 μM | 0.8 | −1.2 | −2.2 |
| Example 21 | 1 μM | 0.0 | 0.6 | −1.2 |
| | 3 μM | 0.0 | −0.3 | −1.6 |
| | 10 μM | 0.1 | 0.4 | −2.0 |
| Comparative example | 1 μM | 2.1 | 7.2 | 1.6 |
| | 3 μM | 18.5 | 34.3 | 10.8 |
| | 10 μM | 51.9 | 35.0 | 17.0 |

The powder X-ray diffraction patterns of the crystals and amorphous substance obtained in Examples 22 to 27 were measured. Such measurement was carried out according to the powder X-ray diffraction measurement method described in General Tests in the Japanese Pharmacopoeia, under the following conditions.

(Apparatus)
Rigaku X-ray DTA System: RINT-2000 (manufactured by Rigaku Corporation)

(Operation Method)
A sample was ground in an agate mortar, and then sampled on a copper board. Thereafter, measurement was carried out under the following conditions.

X-ray used: CuKα ray
Tube voltage: 40 kV
Tube current: 200 mA
Divergent slit: ½ deg
Receiving slit: 0.3 mm
Scattering slit: ½ deg
Scanning rate: 2°/min
Scanning step: 0.02°
Scanning range (2θ): 5° to 40°

The powder X-ray diffraction patterns of the crystals and amorphous substance obtained in Examples 22 to 27 are shown in FIGS. 3 to 8. In addition, the characteristic peaks of diffraction angles (2θ) are summarized in Table 4.

TABLE 4

| Example | Diffraction angle (2θ) |
|---|---|
| 22 | 8.2°, 16.5°, 24.5° |
| 23 | 9.4°, 16.8°, 23.3° |
| 24 | 8.6°, 9.1°, 23.2° |
| 25 | 7.0°, 10.4°, 12.6° |
| 26 | 5.4°, 10.9°, 11.9° |

INDUSTRIAL APPLICABILITY

The present invention provides an agent useful for itch caused by atopic disease or the like.

What is claimed is:

1. A compound represented by the formula (I), salt thereof, or hydrate thereof:

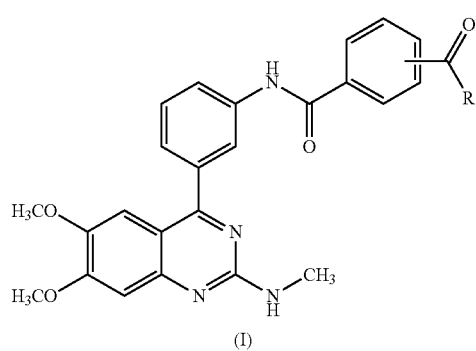

wherein R represents hydroxyl, $C_{1-6}$ alkoxy optionally substituted with $C_{1-6}$ alkoxy, or amino optionally substituted with $C_{1-6}$ alkyl.

2. The compound, salt thereof, or hydrate thereof according to claim 1, wherein R—C(=O)— where R represents hydroxyl, $C_{1-6}$ alkoxy optionally substituted with $C_{1-6}$ alkoxy, or amino optionally substituted with $C_{1-6}$ alkyl is bonded at the meta or para position.

3. The compound, salt thereof, or hydrate thereof according to claim 1, wherein R represents hydroxyl, $C_{1-3}$ alkoxy optionally substituted with $C_{1-3}$ alkoxy, or amino optionally substituted with $C_{1-3}$ alkyl.

4. The compound, salt thereof, or hydrate thereof according to claim 1, wherein R represents hydroxyl, methoxy, ethoxy, 1-propoxy, 2-propoxy, methoxyethoxy, amino, methylamino, dimethylamino, ethylamino, or diethylamino.

5. Methyl N-[3-(6,7-dimethoxy-2-methylaminoquinazolin-4-yl) phenyl]terephthalamic acid, salt thereof, or hydrate thereof, ethyl N-[3-(6,7-dimethoxy-2-methylaminoquinazolin-4-yl)phenyl]terephthalamic acid, salt thereof, or hydrate thereof, N-[3-(6,7-dimethoxy-2-methylaminoquinazolin-4-yl)phenyl]-N'-methylterephthalamide, salt thereof, or hydrate thereof, isopropyl N-[3-(6,7-dimethoxy-2-methylaminoquinazolin-4-yl)phenyl]terephthalamic acid, salt thereof, or hydrate thereof, isopropyl N-[3-(6,7-dimethoxy-2-methylaminoquinazolin-4-yl)phenyl]isophthalic acid, salt thereof, or hydrate thereof, N-[3-(6,7-dimethoxy-2-methylaminoquinazolin-4-yl)phenyl]terephthalamic acid 2-methoxyethyl ester, salt thereof, or hydrate thereof, or N-[3-(6,7-dimethoxy-2-methylaminoquinazolin-4-yl)phenyl]isophthalamic acid 2-methoxyethyl ester, salt thereof, or hydrate thereof.

6. Methyl N-[3-(6,7-dimethoxy-2-methylaminoquinazolin-4-yl) phenyl]terephthalamic acid, salt thereof, or hydrate thereof.

7. Ethyl N-[3-(6,7-dimethoxy-2-methylaminoquinazolin-4-yl) phenyl]terephthalamic acid, salt thereof, or hydrate thereof.

8. N-[3-(6,7-Dimethoxy-2-methylaminoquinazolin-4-yl) phenyl]-N'-methylterephthalamide, salt thereof, or hydrate thereof.

9. Isopropyl N-[3-(6,7-dimethoxy-2-methylaminoquinazolin-4- yl) phenyl]terephthalamic acid, salt thereof, or hydrate thereof.

10. Isopropyl N-[3-(6,7-dimethoxy-2-methylaminoquinazolin-4-yl) phenyl]isophthalic acid, salt thereof, or hydrate thereof.

11. N-[3-(6,7-Dimethoxy-2-methylaminoquinazolin-4-yl) phenyl]terephthalamic acid 2-methoxyethyl ester, salt thereof, or hydrate thereof.

12. N-[3-(6,7-Dimethoxy-2-methylaminoquinazolin-4-yl) phenyl]isophthalamic acid 2-methoxyethyl ester, salt thereof, or hydrate thereof.

13. A method of relieving pruritus in a subject comprising administering the compound, salt thereof, or hydrate thereof according to claim 1.

14. The method according to claim 13, wherein the subject is suffering from atopic disease.

15. The method according to claim 14, wherein the atopic disease is atopic dermatitis.

16. The method according to claim 13, wherein the pruritus is not curable by a steroid drug and/or an anti-histamine agent.

17. The method according to claim 13, wherein the compound, salt thereof, or hydrate thereof is administered in the form of an external preparation.

* * * * *

SEQUENCE LISTING

<160> NUMBER OF SEQ ID NOS: 10

<210> SEQ ID NO 1
<211> LENGTH: 25
<212> TYPE: DNA
<213> ORGANISM: Artificial Sequence
<220> FEATURE:
<223> OTHER INFORMATION: Synthetic forward primer for CYP1A1: hCYP1A1_F1

<400> SEQUENCE: 1
tggtctccct tctctacact cttgt                                         25

<210> SEQ ID NO 2
<211> LENGTH: 31
<212> TYPE: DNA
<213> ORGANISM: Artificial Sequence
<220> FEATURE:
<223> OTHER INFORMATION: Synthetic reverse primer for CYP1A1: hCYP1A1_R1

<400> SEQUENCE: 2
attttcccta ttacattaaa tcaatggttc t                                  31

<210> SEQ ID NO 3
<211> LENGTH: 21
<212> TYPE: DNA
<213> ORGANISM: Artificial Sequence
<220> FEATURE:
<223> OTHER INFORMATION: Synthetic forward primer for CYP1A2:
      hCYP1A2_F_EJCP

<400> SEQUENCE: 3
gttcctgcag aaaacagtcc a                                             21

<210> SEQ ID NO 4
<211> LENGTH: 19
<212> TYPE: DNA
<213> ORGANISM: Artificial Sequence
<220> FEATURE:
<223> OTHER INFORMATION: Synthetic reverse primer for CYP1A2:
      hCYP1A2_R_EJCP

<400> SEQUENCE: 4
ctgtgcttga acagggcac                                                19

<210> SEQ ID NO 5
<211> LENGTH: 33
<212> TYPE: DNA
<213> ORGANISM: Artificial Sequence
<220> FEATURE:
<223> OTHER INFORMATION: Synthetic probe for CYP1A2: hCYP1A2_probe_EJCP

<400> SEQUENCE: 5
agcactatca ggactttgac aagaacagtg tct                                33

<210> SEQ ID NO 6
<211> LENGTH: 22
<212> TYPE: DNA
<213> ORGANISM: Artificial Sequence
<220> FEATURE:
<223> OTHER INFORMATION: Synthetic forward primer for CYP3A4:
      hCYP3A4_F_m

```
<400> SEQUENCE: 6
gcaggaggaa attgatgcag tt                                              22

<210> SEQ ID NO 7
<211> LENGTH: 27
<212> TYPE: DNA
<213> ORGANISM: Artificial Sequence
<220> FEATURE:
<223> OTHER INFORMATION: Synthetic reverse primer for CYP3A4:
      hCYP3A4_R_x

<400> SEQUENCE: 7
gtcaagatac tccatctgta gcacagt                                         27

<210> SEQ ID NO 8
<211> LENGTH: 27
<212> TYPE: DNA
<213> ORGANISM: Artificial Sequence
<220> FEATURE:
<223> OTHER INFORMATION: Synthetic probe for CYP3A4: hCYP3A4_probe_m

<400> SEQUENCE: 8
acccaataag gcaccaccca cctatga                                         27

<210> SEQ ID NO 9
<211> LENGTH: 19
<212> TYPE: DNA
<213> ORGANISM: Artificial Sequence
<220> FEATURE:
<223> OTHER INFORMATION: Synthetic forward primer for GAPDH: hGAPDH_F

<400> SEQUENCE: 9
gaaggtgaag gtcggagtc                                                  19

<210> SEQ ID NO 10
<211> LENGTH: 20
<212> TYPE: DNA
<213> ORGANISM: Artificial Sequence
<220> FEATURE:
<223> OTHER INFORMATION: Synthetic reverse primer for GAPDH: hGAPDH_R

<400> SEQUENCE: 10
gaagatggtg atgggatttc                                                 20
```